US008717574B2

(12) United States Patent
Yang et al.

(10) Patent No.: US 8,717,574 B2
(45) Date of Patent: May 6, 2014

(54) TURBIDITY SUPPRESSION BY OPTICAL PHASE CONJUGATION USING A SPATIAL LIGHT MODULATOR

(75) Inventors: Changhuei Yang, Pasadena, CA (US); Meng Cui, Ashburn, VA (US)

(73) Assignee: California Institute of Technology, Pasadena, CA (US)

( * ) Notice: Subject to any disclaimer, the term of this patent is extended or adjusted under 35 U.S.C. 154(b) by 635 days.

(21) Appl. No.: 12/943,857

(22) Filed: Nov. 10, 2010

(65) Prior Publication Data

US 2011/0122416 A1 May 26, 2011

Related U.S. Application Data

(60) Provisional application No. 61/259,975, filed on Nov. 10, 2009, provisional application No. 61/260,316, filed on Nov. 11, 2009, provisional application No. 61/376,202, filed on Aug. 23, 2010, provisional application No. 61/355,328, filed on Jun. 16, 2010.

(51) Int. Cl.
*G01B 9/021* (2006.01)

(52) U.S. Cl.
USPC ............................................... 356/457

(58) Field of Classification Search
USPC ............................................... 356/457
See application file for complete search history.

(56) References Cited

U.S. PATENT DOCUMENTS

| 4,866,781 A | 9/1989 | Borken et al. |
| 4,928,695 A | 5/1990 | Goldman et al. |
| 5,760,388 A | 6/1998 | Swandic |
| 6,115,123 A * | 9/2000 | Stappaerts et al. ............ 356/457 |
| 7,027,161 B2 * | 4/2006 | Pepper ........................... 356/450 |
| 7,119,906 B2 * | 10/2006 | Pepper et al. ................. 356/484 |
| 2002/0057486 A1 | 5/2002 | Tanaka |
| 2004/0125380 A1 | 7/2004 | Pepper |
| 2009/0009834 A1 | 1/2009 | Yaqoob et al. |

OTHER PUBLICATIONS

Fink, M., "Time-reversed acoustics," Scientific American, vol. 281, pp. 91-97, Nov. 1999.
Vo-Dinh, T., *Biomedical Photonics Handbook*, Boca Raton, Florida: CRC Press 2003, copyright and table of contents.
Yeh, P., *Introduction to Photorefractive Nonlinear Optics*, John Wiley & Sons, Inc., New York, 1993, copyright and table of contents.
Gower, D., *Optical Phase Conjugation* (Springer-Verlag, New York, 1994) copyright and table of contents.
Boas, D. et al., "Imaging the body with diffuse optical tomography," IEEE Signal Processing, vol. 18, pp. 57-75, 2001.
Booth, M. et al., "Adaptive aberration correction in a confocal mircoscope," PNAS, vol. 99, No. 9, 5788-5792, Apr. 30, 2002.
Cui, M. et al., "An in vivo study of turbidity suppression by optical phase conjugation (TSOPC) on rabbit ear," Optics Express 18, No. 1, Jan. 4, 2010, 25.
Cui, M. et al., "Implementation of a digital optical phase conjugation system and its application to study the robustness of turbidity suppression by phase conjugation," Optics Express 18, No. 4, Feb. 15, 2010, 3444.

(Continued)

*Primary Examiner* — Tarifur Chowdhury
*Assistant Examiner* — Jonathon Cook
(74) *Attorney, Agent, or Firm* — Gates & Cooper LLP

(57) ABSTRACT

A detector of light transmitted through a turbid medium, comprising: one or more Digital Optical Phase Conjugation (DOPC) devices, wherein the DOPC devices include (1) a sensor for detecting input light that has been transmitted through the turbid medium and inputted on the sensor; and (2) a spatial light modulator (SLM) for outputting, in response to the input light detected by the sensor, output light that is an optical phase conjugate of the input light.

26 Claims, 16 Drawing Sheets

(56) References Cited

OTHER PUBLICATIONS

Cui, M. et al., "Observation of polarization-gate based reconstruction quality improvement during the process of turbidity suppression by optical phase conjugation," Applied Physics Letters 95, 123702 (2009).
Cui, X. et al., "Lensless high-resolution on-chip optofluidic microscopes for *Caenorhabditis elegans* and cell imaging," PNAS, vol. 105, No. 31, Aug. 5, 2008, 10670-10675.
Debarre, D. et al., "Adaptive optics for structured illumination microscopy," Optics Express 16, No. 13, Jun. 23, 2008, 9290.
Debarre, D. et al., "Image-based adaptive optics for two-photo microscopy," Optics Letters, vol. 34, No. 16, Aug. 15, 2009, 2495.
Derode, A. et al., "Random multiple scattering of ultrasound. II. Is time reversal a self-averaging process?," Physical Review E, vol. 64, 2001, 036606.
Dougherty, T. et al., "Photodynamic therapy," Journal of the National Cancer Institute, vol. 90, No. 12, Jun. 17, 1998, 889.
Feinberg, J. et al., "Phase-conjugating mirror with continuous-wave gain," Optics Letters, vol. 5, No. 12, Dec. 1980, 519.
Fink, M., "Time reversed acoustics," Physics Today 50(3), 34-40 (1997).
Goodman, J., "Some fundamental properties of speckle," J. Opt. Soc. Am., vol. 66, No. 11, Nov. 1976, 1145.
Hayden, E., "Microscopic marvels: Microscope for the masses," Nature, vol. 459, p. 632, 2009.
Hell, S. et al., "Properties of a 4Pi confocal fluorescence microscope," J. Opt. Soc. Am. A, vol. 9, No. 12, Dec. 1992, 2159.
Huang, D. et al., "Optical coherence tomography," Science, vol. 254, Nov. 22, 1991, 1178.
Hyde, S. et al., "Depth-resolved holography through turbid media using photorefraction," IEEE Journal of Selected Topics in Quantum Electronics, vol. 2, No. 4, Dec. 1996, 965.
Kawata, Y. et al., "4Pi confocal optical system with phase conjugation," Optics Letters 21, No. 18, Sep. 15, 1996, 1415.
Leith, E. et al., "Holographic imagery through diffusing media," Journal of the Optical Society of America, vol. 56, No. 4, Apr. 1966, 523.
Lind, R. et al., "Demonstration of the longitudinal modes and aberration-correction properties of a continuous-wave dye laser with a phase-conjugate mirror," Optics Letters 6, No. 11, Nov. 1981, 554.
Lindsay, I., "Specular reflection cancellation/enhancement in the presence of a phase-conjugate mirror," J. Opt. Soc. Am. B, vol. 4, No. 11, Nov. 1987, 1810.
Pepper, D., "Observation of diminished specular reflectivity from phase-conjugate mirrors," Physic Review Letters, vol. 62, No. 25, Jun. 19, 1989, 2945.
Primmerman, C. et al., "Compensation of atmospheric optical distortion using a synthetic beacon," Letters to Nature, vol. 353, Sep. 12, 1991, 141.
Ridley, K. et al., "Incomplete phase conjugation through a random phase screen. II. Numerical simulations," J. Opt. Soc. Am. A, vol. 13, No. 12, Dec. 1996, 2393.
Rueckel, M. et al., "Adaptive wavefront correction in two-photon microscopy using coherence-gated wavefront sensing," PNAS, vol. 103, No. 46, Nov. 14, 2006, 17137-17142.
Vellekoop, I. et al., "Demixing light paths inside disordered metamaterials," Optics Express 16, No. 1, Jan. 7, 2008, 67.
Vellekoop, I. et al., Focusing coherent light through opaque strongly scattering media, Optics Letters 32, No. 16, Aug. 15, 2007, 2309.
Vellekoop, I. et al., "Universal optical transmission of light through disordered materials," Physical Review Letters 101, 120601 (2008).
Wang, L., "Multiscale photoacoustic microscopy and computer tomography," Nature Photonics, vol. 3, Sep. 2009, 503.
Wang, L. et al., "Ultrasound-modulated optical tomography of absorbing objects buried in dense tissue-simulating turbid media," Applied Optics 36, No. 28, Oct. 1, 1997, 7277.
Wenner, M., "The most transparent research," Nat. Med. 15(10), 1106-1109 (2009).
Yamaguchi, I., "Phase-shifting digital holography," Optics Letters 22, No. 16, Aug. 15, 1997, 1268.
Yariv, A., "Phase conjugate optics and real-time holography," IEEE Journal of Quantum Electronics, vol. QE-14, No. 9, Sep. 1978, 650.
Zhang, T., "Three-dimensional microscopy with phase-shifting digital holography," Optics Letters 23, No. 15, Aug. 1, 1998, 1221.
International Search Report mailed Aug. 31, 2011, International application No. PCT/US2010/056274, International filing date Nov. 10, 2010.
McDowell, E. et al., "A proposed deep tissue imaging scheme based on turbidity suppression optical phase conjugation," Biomedical Optics (BIOMED), Mar. 16, 2008, BIOMED Poster Session I.
Yaqoob, Z. et al., "Optical phase conjugation for turbidity suppression in biological samples," Nature Photonics, vol. 2, Feb. 2008, 110.

* cited by examiner

TURBIDITY SUPPRESSION BY OPTICAL PHASE CONJUGATION USING A SPATIAL LIGHT MODULATOR

CROSS REFERENCE TO RELATED APPLICATIONS

This application claims the benefit under 35 U.S.C. §119 (e) of the following co-pending and commonly-assigned U.S. provisional patent applications, which are incorporated by reference herein:

Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES";

Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION";

Provisional Patent Application Ser. No. 61/376,202, filed on Aug. 23, 2010, by Meng Cui and Changhuei Yang, entitled "OPTICAL PHASE CONJUGATION 4PI MICROSCOPE"; and Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY".

This application is related to the following co-pending and commonly-assigned U.S. patent applications, which are incorporated by reference herein:

U.S. Utility patent application Ser. No. 12/886,320, filed on Sep. 20, 2010, now U.S. Pat. No. 8,525,998 issued on Sep. 3, 2013, by Zahid Yaqoob, Emily McDowell and Changhuei Yang, entitled "OPTICAL PHASE PROCESSING IN A SCATTERING MEDIUM", which application is a divisional of U.S. Utility patent application Ser. No. 11/868,394, filed on Oct. 5, 2007, by Zahid Yaqoob, Emily McDowell and Changhuei Yang, entitled "TURBIDITY ELIMINATION USING OPTICAL PHASE CONJUGATION AND ITS APPLICATIONS", which application claims priority under 35 U.S.C. §119(e) to commonly-assigned U.S. Provisional Patent Application Ser. No. 60/850,356, filed on Oct. 6, 2006, by Zahid Yaqoob, Emily McDowell and Changhuei Yang, entitled "TURBIDITY ELIMINATION USING OPTICAL PHASE CONJUGATION AND ITS APPLICATIONS";

U.S. Utility application Ser. No. 12/943,841, filed on Nov. 10, 2010, now U.S. Pat. No. 8,450,674 issues on May 28, 2013, by Meng Cui, Ying Min Wang, Changhuei Yang and Charles DiMarzio, entitled "ACOUSTIC ASSISTED PHASE CONJUGATE OPTICAL TOMOGRAPHY," which application claims priority under 35 U.S.C. §119(e) to co-pending and commonly-assigned U.S. Provisional Application Ser. No. 61/355,328, filed on Jun. 16, 2010, by Meng Cui, Ying Min Wang, and Changhuei Yang, entitled "ACOUSTIC ASSISTED PHASE CONJUGATE OPTICAL TOMOGRAPHY"; U.S. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES"; U.S. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION"; and U.S. Provisional Patent Application Ser. No. 61/376,202, filed on Aug. 23, 2010, by Meng Cui and Changhuei Yang, entitled "OPTICAL PHASE CONJUGATION 4PI MICROSCOPE"; and U.S. Utility application Ser. No. 12/943,818, filed on Nov. 10, 2010, by Meng Cui and Changhuei Yang, entitled "OPTICAL PHASE CONJUGATION 4PI MICROSCOPE," which application claims priority under 35 U.S.C. §119(e) to co-pending and commonly-assigned U.S. Provisional Application Ser. No. 61/376,202, filed on Aug. 23, 2010, by Meng Cui and Changhuei Yang, entitled "OPTICAL PHASE CONJUGATION 4PI MICROSCOPE"; U.S. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES"; U.S. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION"; and U.S. Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY;".

STATEMENT REGARDING FEDERALLY SPONSORED RESEARCH AND DEVELOPMENT

This invention was made with Government support under Grant No. R21EB008866-02 awarded by NIH. The Government has certain rights in this invention.

BACKGROUND OF THE INVENTION

1. Field of the Invention

The present invention relates generally to turbidity suppression by optical phase conjugation using a spatial light modulator.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

In general, biological tissues are highly turbid media in the optical regime [1]. The extensive scattering of light by tissue is a significant obstacle for deep-tissue optical imaging and optical sensing [2]. In recent years, several publications [3-6] have reported that it is experimentally possible to mitigate the effects of scattering by tailoring an input light field wavefront appropriately. For example, Mosk's group showed that it is possible to focus light through a scattering medium by modifying and optimizing the wavefront of an input light field with a spatial light modulator [3,5]. Our group showed that an optical phase conjugate (OPC) copy of an initial transmission through a biological sample can likewise undo the effects of the initial scattering [4,7,8].

Employing optical phase conjugation to suppress tissue turbidity as described in embodiments of the present invention is appealing because it simply requires the duplication of a transmission light field for which the phase at each point on the wavefront is sign-reversed. Optical phase conjugation (OPC) has been an active field since the 1970s and has produced numerous applications including novel resonators, high-resolution image projection, and optical computing devices [9-15]. The generation of the OPC wave was based on optical nonlinearities such as photorefractive effect [14] and Brillouin scattering [15]. OPC based on nonlinear light-matter interactions can handle a large number of optical degrees of freedom. However, the nonlinear optics based OPC techniques often provide limited phase conjugation reflectivity, defined as the power ratio of the phase conjugate signal to the input signal. In addition, specialized light source and nonlinear media are usually required [15]. For practical purposes, an OPC system that can work with various light sources of different wavelengths, coherence lengths, and power levels would be preferable.

Another promising class of optical methods is adaptive optics. In adaptive optics, a wavefront sensor and modulator are used to measure and compensate for phase aberration. Adaptive optics techniques were originally developed to compensate for atmospheric distortion in astronomical telescopes [16]. In the past two decades, several research teams have employed adaptive optics techniques to compensate for the aberration in the optical microscopy systems and the aberration induced by the refractive index variation in the specimen [17-19]. The amount of aberration in these applications is fairly limited and can often be decomposed to several orders of Zernike polynomials [17-20]. In such cases, deformable mirrors are often employed as the wavefront modulator to provide adequate aberration compensation. Recently Mosk's team has successfully demonstrated a pixel by pixel optimization method to form an optical focus through highly turbid samples ($\mu_s l$ ~10, $\mu_s$, scattering coefficient, l, sample thickness) by using high capacity spatial light modulators [3].

In view of the above, what is needed is the capability to mitigate the effects of scattering in a highly turbid media in a robust manner that can accommodate phase errors.

SUMMARY OF THE INVENTION

One or more embodiments of the invention provide a high capacity (number of degrees of freedom) open loop adaptive optics method, termed digital optical phase conjugation (DOPC), that provides a robust optoelectronic optical phase conjugation (OPC) solution. Conjugate light fields can be phased with ~$3.9 \times 10^{-3}$ degree accuracy over a range of ~3 degrees and an input field can be phase conjugated through a relatively thick turbid medium ($\mu_s l$ ~13, wherein $\mu_s l$ is average number of scattering events, $\mu_s$ is scattering coefficient and l is path length). Furthermore, embodiments show that the reversing of random scattering in turbid media by phase conjugation is surprisingly robust and accommodating of phase errors. An OPC wavefront with significant spatial phase errors (error uniformly distributed from $-\pi/2$ to $\pi/2$) can nevertheless allow OPC reconstruction through a scattering medium with ~40% of the efficiency achieved with phase error free OPC.

Thus, to overcome the limitations in the prior art, and to overcome other limitations that will become apparent upon reading and understanding the present specification, the present invention discloses a detector of transmitted light that has been transmitted through a turbid medium, comprising one or more Digital Optical Phase Conjugation (DOPC) devices, wherein the DOPC devices include (1) a sensor for detecting input light that has been transmitted through the turbid medium and inputted on the sensor; and (2) a spatial light modulator (SLM) for outputting, in response to the input light detected by the sensor, output light that is an optical phase conjugate of the input light.

The transmitted light may include the output light and the input light, the detector further comprising a holder for supporting the turbid medium and positioned such that the transmitted light is transmitted through the turbid medium, wherein the output light that has been transmitted through the turbid medium, and that has retraced a path of the input light through the turbid medium, experiences reduced effects due to scattering by the turbid medium as compared to the input light.

The DOPC devices may include a first DOPC device and a second DOPC device, wherein the DOPC devices and the holder are positioned such that the transmitted light propagates between the first DOPC device and the second DOPC device and passes through the turbid medium each time the transmitted light propagates between the first DOPC device and the second DOPC device, and the output light from the first DOPC is inputted as the input light to the second DOPC device.

The DOPC devices and the holder may be positioned such that the output light from the second DOPC device is inputted as the input light to the first DOPC device.

The detector may further comprise one or more processors connected to the DOPC devices for calculating absorption and transmission of the transmitted light after one or more passes of the transmitted light through the turbid medium, wherein the absorption and the transmission is calculated from one or more input light fields of the input light and one or more output light fields of the output light detected by the DOPC devices. The processors may calculate the absorption and the transmission of the transmitted light that made n passes through the turbid medium, where n is a number of passes that yields between 40% and at least 66% transmission of the transmitted light as compared to an $(n-1)^{th}$ pass and for a turbid medium that does not absorb the transmitted light.

The turbid medium may be biological tissue and the one or more processors calculate the absorption of the transmitted light as a function of one or more wavelengths of the transmitted light, wherein (1) the absorption is for matching with data in a database, the data including known absorption as a function of wavelength for one or more medically relevant biochemicals, and (2) the matching identifying an amount of the medically relevant biochemicals in the biological tissue.

The detector may further comprise a beam splitter positioned to direct the input light, and transmit reference light, to the sensor so that the input light and the reference light interferes and forms one or more holograms on the sensor, the holograms comprising interferometric data; and one or more processors for receiving the interferometric data and determining input phases and input amplitudes of input light fields of the input light from the inteferometric data; digitally modifying the input phases and the input amplitudes to produce modified input phases and modified input amplitudes; and outputting the modified input phases and modified input amplitudes to the SLM and so that the SLM outputs the output light having the modified input phases and modified input amplitudes that are the optical phase conjugates of the input phases and the input amplitudes.

The detector may further comprise an electro-optic modulator that controls a relative phase between the input light fields of the input light and reference fields of the reference light, so that the holograms include one or more phase shifted holograms.

The sensor may comprise a plurality of sensor pixels, the SLM may comprise a plurality of SLM pixels forming a second array, and the sensor and the SLM may be optically aligned so that each sensor pixel forms a virtual image of the sensor pixel on a corresponding SLM pixel.

Embodiments of the present invention may perform biochemical analysis without blood draw. Embodiments of the present invention may also dramatically improve high-resolution microscopy techniques for bioscience research by tackling the challenge of sample scattering head-on. Further, less intrusive deep tissue light-based therapeutic procedures may be provided.

BRIEF DESCRIPTION OF THE DRAWINGS

Referring now to the drawings in which like reference numbers represent corresponding parts throughout:

FIG. 1(a)-(c) illustrate that scattering according to one or more embodiments of the present invention may appear random but it is a deterministic process, wherein FIG. 1(a) illustrates collecting and time-reversing the diffuse light transmission through tissues, FIG. 1(b) illustrates recovering the original input light field, wherein the effect is attributable to the wave nature of light, and FIG. 1(c) illustrates the diffusive effect of light scattering, showing that red light transmits more easily than green or blue light;

FIG. 2(b) illustrates a 0.5 mm thick tissue significantly scatters and diffuses the original light field, FIG. 2(c) illustrates an ability to holographically record the transmission, FIG. 2(d) illustrates playing back a time reversed or OPC field by reading out the recording with an appropriate readout field, wherein the transmission accurately reconstructs the original input field, and FIG. 2(e) illustrates that when shifting the tissue during the playback process, the time-reversed light field may no longer be able to retrace its path and the reconstruction disappears;

FIG. 4(a)-(b) are schematics illustrating that the two elements of the DOPC system, according to one or more embodiments of the present invention, comprise a wavefront measurement device (sensor) and a spatial light modulator (actuator), are optically combined with a beam splitter and function as a single system that can both measure an input wavefront and generate a phase conjugate output wavefront, wherein FIG. 4(a) shows the wavefront measurement process wherein a reference wave interferes with the input signal, wherein their relative phase is controlled by an EO phase modulator, and FIG. 4(b) shows the phase shaping process wherein the SLM modulates the incident reference wave;

FIG. 6(b) shows a phase pattern that was displaced on the SLM, that was imaged on CCD 2, FIG. 6(c) illustrates that the mask was illuminated and imaged on CCD 2, FIG. 6(d) illustrates an experimentally measured SLM image, and FIG. 6(e) illustrates an experimentally measured mask image;

FIG. 10(b) illustrates the DOPC reconstructed signal, wherein the field of view is ~12 µm, and FIG. 10 (c) illustrates control measurement with the phase of the SLM set to 0, according to one or more embodiments of the present invention;

FIG. 12 illustrates an iterative TSOPC transmission sensing scheme, according to one or more embodiments of the present invention, wherein FIG. 12(a) illustrates recording initial transmission on DOPC1, FIG. 12(b) illustrates playback OPC field and record transmission on DOPC2, FIG. 12 (c) illustrates playback of new OPC field and record transmission on DOPC1, wherein embodiments of the present invention may iterate between the steps of FIG. 12(b) and FIG. 12(c) to optimize tissue transmission through the 'open channels' and transmission loss is then attributable to absorption;

FIG. 15(b) illustrates a 4Pi microscope that uses 2 counter-propagating focused laser beams to generate interference axially to improve axial resolution (~120 nm), FIG. 15 (c) illustrates a 4Pi microscope that performs poorly for thick tissue sections because scattering diffuses the laser beam spots, wherein, at superficial depths, 4Pi microscope's axial resolution is comparable to a confocal microscope because one beam is too diffused to be helpful, FIG. 15 (*d*) illustrates an OPC 4Pi microscope of embodiments of the present invention that combine one of the objectives with a DOPC system, wherein the OPC field thus generated is always an exact match for the tightly focused laser beam propagating downwards, and FIG. 15 (*e*) illustrates an OPC 4Pi microscope that works well with thick tissue sections because the OPC field will undo the effects of scattering, wherein the penetration depth may be limited (comparable to confocal) because the initial laser beam may not be able to come to a tight focus if the amount of scattering experienced by the beam is too great.

DETAILED DESCRIPTION OF THE INVENTION

Figure 1:
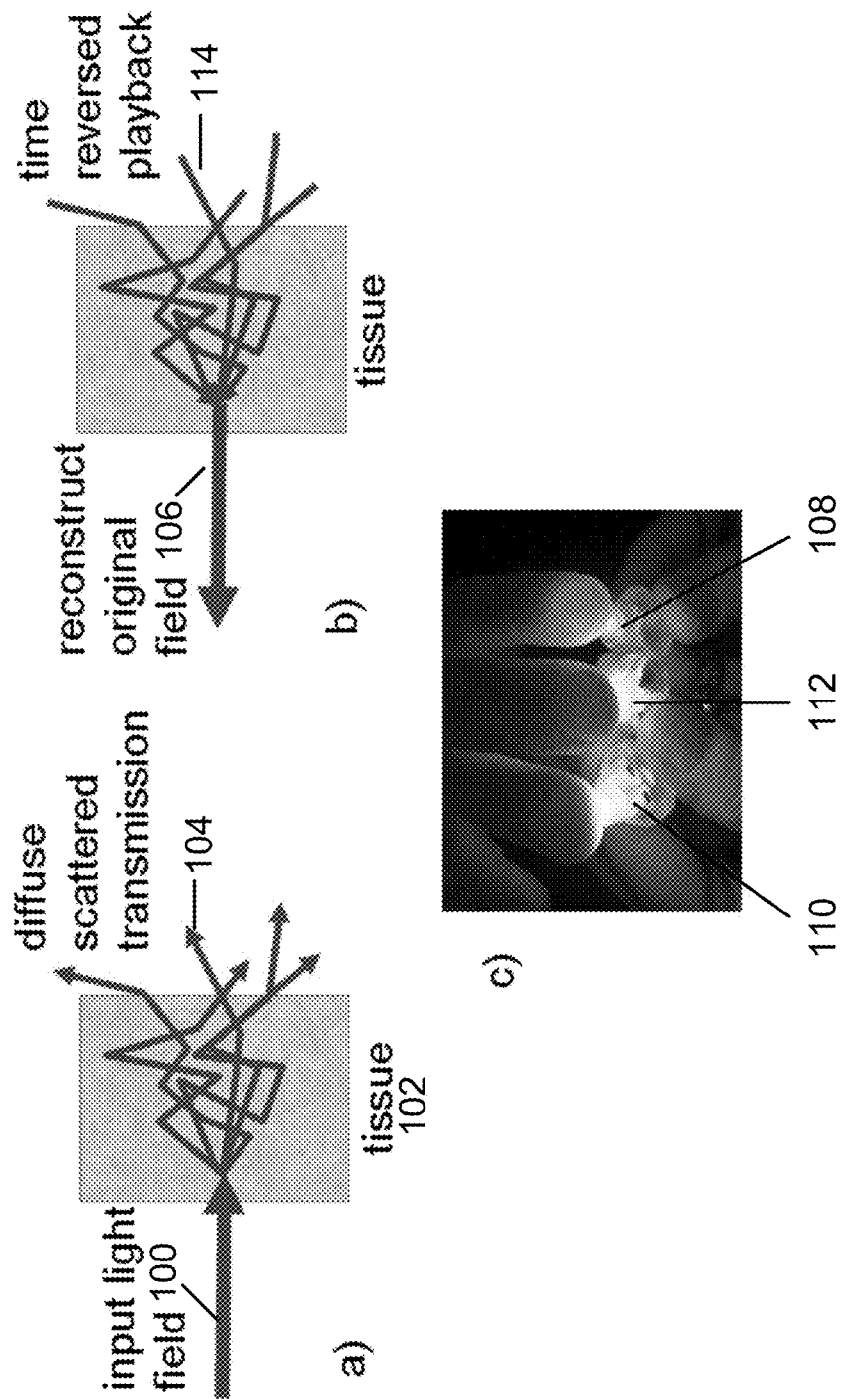

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Overview

Embodiments of the present invention disclose the use of time-reversal optical techniques to induce a limited form of tissue transparency by suppressing optical scattering and to apply the findings to develop new and improved classes of optical microscopy, biosensing and optical therapeutic techniques. Recent discoveries provide that time-reversed photons can retrace their scattering trajectories through biological tissues and that this phenomenon is surprisingly robust [21, 22]. This phenomenon is termed "tissue turbidity suppression by optical phase conjugation (TSOPC)".

One may better understand and appreciate the potential impacts that this phenomenon can have in biomedicine by first taking a closer look at optical tissue scattering. In general, biological tissues are highly scattering or turbid in the optical regime. In fact, light scattering is typically 2-3 orders of magnitude stronger than light absorption in tissues. In very much the same way that fog diffuses a car headlight, tissue will deflect an incident light beam in a multitude of directions. The greater the tissue turbidity and/or tissue thickness, the more diffused the light beam becomes. If one can turn off tissue turbidity, the human body would take on the appearance of a large jellyfish mass, performing spectroscopy-based biochemical analysis non-invasively could be straightforward, delivering light deep into tissues for therapeutic purposes will be possible, and optically imaging through thicker tissue sections is feasible. Thus, tissue scattering is a significant problem for a broad range of biophotonics technologies.

Embodiments of the present invention apply TSOPC to design and implement new optical biomedical tools, including high-sensitivity in-vivo biochemical (such as glucose) sensors, high-resolution and deeper penetrating microscopes, and deep tissue therapeutic light delivery systems. These applications are developed in a synergistic fashion. This new way of tackling optical tissue turbidity head-on leads to new ways to use light for biomedicine.

Embodiments of the present invention briefly outline the ways that tissue scattering limits current optical biomedicine techniques, describes findings on TSOPC, and discloses the robustness and ways this effect can be applied to improve biomedicine. Furthermore, embodiments of the invention disclose new TSOPC-based biomedical tools.

Technical Description

Tissue Scattering Limits on Current Optical Biomedicine Techniques.

Elastic optical scattering in biological tissues is typically stronger than absorption by a few orders of magnitude. As a point of reference, light propagation in human dermis at a wavelength 633 nm is characterized by a mean scattering length of 35 microns (average path length traveled by a photon between scattering events) and a mean absorption length of 3 mm [25].

During the transmission through biological tissues, light generally traces meandering paths through the medium and exits the tissues in multiple directions. If the ratio of tissue thickness to mean scattering length is large, most of the light may never make it to the other side of the tissue and would instead be backscattered by the tissue. Although the spectral properties and angular profiles of scattered light can reveal useful physiological information about a given tissue sample, light scattering is generally regarded as a deleterious process that drastically complicates and limits biophotonic applications.

Optical biomedical technologies employ a number of strategies to address this issue. Embodiments of the present invention look at three main approaches.

1) Employing longer optical wavelengths. In general, biological tissues mean scattering lengths are longer and the scattered light is more forward-directed for longer optical wavelengths. The pulse oximeter is a good example of a medical device that employs this strategy to ensure good light transmission through tissue for sufficiently sensitive absorption measurements. However, this strategy is limited because water (the main constituent of tissues) absorption increases dramatically for longer wavelengths. At a wavelength of 2.5 microns, the mean absorption length for water reaches 10 microns and effectively erases any gains against scattering.

2) Selectively detecting unscattered or singly scattered light components during the detection process. These light components trace straight paths through tissues and are easily analyzed. Optical coherence tomography [26]—an optical equivalence of ultrasound imaging—employs this strategy via interferometry to perform high-resolution imaging in tissues to a depth of ~1 mm. However, this strategy cannot be extended to arbitrary depths as the amount of unscattered light becomes ever rarer with greater depth (exponential decrease).

3) Applying computational models to account for scattering. Optical diffuse tomography [27] employs this approach to process large sets of diffuse light transmission data to render coarse resolution images of absorption sites in tissues. This approach is computationally intensive and often plagued by ill-posed measurement conditions.

Notably, scattering is not a significant problem for most non-optical bio-imaging modalities. For example, ultrasound imaging employs acoustic waves and x-ray imaging employs high-energy electromagnetic waves; both operate in regimes where the effective scattering lengths are long. These considerations prompt the question of why embodiments of the present invention should bother with optical based biosensing and bioimaging methods at all. The answer lies in the fact that there exists a wealth of light-matter interaction mechanisms in the optical regime. A photon's energy is on the same order of magnitude as the step sizes between the atoms' and molecules' electronic level. As such, molecules can absorb light, fluoresce and emit Raman light with distinct spectral characteristics. By detecting these spectral variations, we can measure the biochemical content of tissues optically. The ability of optical methods to sense biochemicals is an especially important one.

Tissue Turbidity Suppression By Optical Phase Conjugation (TSOPC)

FIG. 1(a)-(c) illustrate that while elastic scattering of an input optical light field 100 by biological tissues 102 may appear random, it is actually and fundamentally a deterministic and time reversible process. If the present invention collects and time-reverses the diffuse light transmission 104 through tissues 100, embodiments of the present invention can recover or reconstruct the original input light field 106, a shown in FIG. 1(b). This effect is attributable to the wave nature of light. FIG. 1(c) illustrates the diffusive effect of light scattering, wherein red light 108 transmits more easily than green light 110 or blue light 112. FIG. 1(c) also illustrates that if the ratio of tissue thickness to mean scattering length is large, most of the light may never make it to the other side of the tissue 102 and would instead be backscattered by the tissue 102.

In other words, if the phase and amplitude of the propagating scattered light field 104 is completely recorded and used to reproduce a back propagating optical phase conjugate (OPC) or time-reversed play back field 114, this field would retrace its trajectory through the scattering medium and return the original input light field 106. The ability of a time-reversed light field to undo the effects of scattering is well known in the physics community and it has been demonstrated to work with distorting glass plates [23] and has been applied to improve laser performance. However, embodiments of the present invention are the first to adapt the concept to suppress tissue scattering [21]. Experiments further demonstrate that the phenomenon is surprisingly robust—one can observe the effect in living tissues and through tissues that are so thick that each photon is scattered >200 times on average.

This new way of tackling tissue scattering is unusually innovative as it represents a big departure from the ways current optical techniques address tissue scatterings (a recent Nature Medicine article showcased some unique aspects of TSOPC [24]). In general, existing techniques either choose to work at optical wavelengths where scattering is less significant, or selectively gate out multiple scattered photons, or apply post-measurement modeling to correct for scattering effects. TSOPC actually allows the direct suppression of tissue scattering.

There exist numerous optical methods by which an OPC field can be generated—four wave mixing, holography and photorefraction. The holography approach is straightforward. For this method, light passes through the tissue and records the scattered light field on a holographic plate with the help of a reference writing beam. Once the recording has been made, a back-propagating OPC field is generated by illuminating the plate with an appropriate readout beam. This OPC field should be able to retrace the original light field's paths through the scattering medium and reconstruct the original light beam. A photorefractive crystal—a rewritable holographic material—can be substituted without significant modifications.

Figure 2:
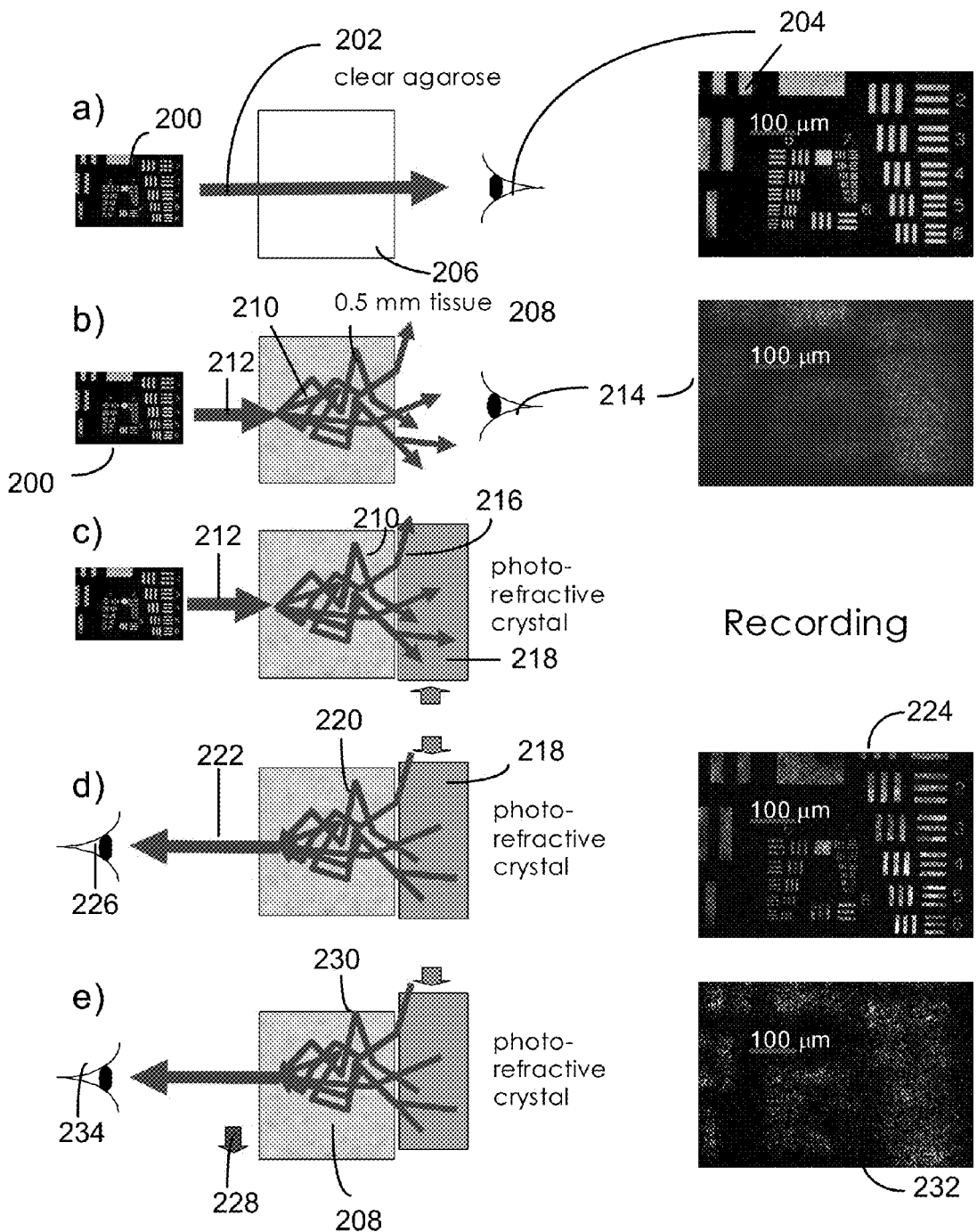
FIG. 2(a)-(e) demonstrates TSOPC according to one or more embodiments of the present invention, wherein in FIG. 2(a) shows an image bearing light field can be clearly imaged through a clear medium.

FIG. 2(a) shows an image 200 bearing light field 202 can be clearly imaged 204 through a clear medium 206 (e.g., clear agarose).

FIGS. 2(b)-(e) demonstrate that TSOPC can be easily observed using one or more embodiments of the present invention.

FIG. 2(b) illustrates that a 0.5 mm thick tissue 208 significantly scatters 210 and diffuses the original light field 212, so that the image 200 cannot be clearly viewed 214 through the tissue 208.

FIG. 2(c) shows the ability to holographically record the transmission 216 using a photorefractive crystal 218 in accordance with one or more embodiments of the invention.

FIG. 2(d) illustrates play back of a time reversed or OPC field 220 by reading out the recording with an appropriate readout field. The transmission 222 accurately reconstructs the original input field, so that the image 200 is clearly reproduced 224 when viewed 226 through the tissue 208.

FIG. 2(e) illustrates that when embodiments of the present invention shift or displace 228 the tissue 208 during the playback process, the time-reversed light field 230 would no longer be able to retrace their paths and the reconstruction 232 disappears or no longer appears (image can no longer be viewed 234 through the tissue 208). This further shows that the observed reconstruction was due to path retracing.

The results in FIG. 2(b)-(e) were obtained with a tissue section 208 that was of sufficient thickness (e.g., 0.5 mm thickness) to scatter each photon an average of 20 times during its passage.

Subsequent experiments have revealed that this phenomenon is surprisingly robust.

One can observe the TSOPC effect through a tissue section (e.g., chicken tissue 300) of thickness 7 mm and using an input light field wavelength of 532 nm, as shown in FIG. 3(a). The left hand photo in FIG. 3(a) shows the tissue 300 displaced, leading to no TSOPC effect, and the right hand photo in FIG. 3(a) shows no displacement of the tissue 300, so that TSOPC is observed.

FIG. 3(b) shows TSOPC reconstruction of a light spot 302 through the tissue section 300 of FIG. 3(a), wherein the left hand image in FIG. 3(b) shows the results for the sample 300 displaced by 5 micrometers (no spot observable) and the right hand image in FIG. 3(b) shows the TSOPC signal for no displacement, wherein the light spot 302 is clearly visible through the tissue 300.

At those parameter choices, each photon experienced over 200 scattering events on average. Perhaps more interestingly, the fraction of scattering wavefront recorded and played back was only 0.02% of the total and, yet, the TSOPC effect was still observable, albeit the efficiency of the reconstruction was measurably lower. This result was surprising because one would intuitively expect that this type of inversion process should depend critically on the full collection and playback of the entire wavefront. Remarkably, the TSOPC effect is sufficiently robust and capable of withstanding the underdetermined nature of the playback process. Practically, this bodes well for the adaptation of the TSOPC effect for biomedical applications as experimental results imply that the implementation conditions are far less stringent and exacting than one might otherwise expect.

The blood flow, cellular movements and Brownian motions within tissues can be expected to disrupt the light field path retracing process—scatterers' displacements between the forward transmission and backward playback process necessarily break the inversion process. To determine the speed by which such disruption occurs, an experiment with a living rabbit ear can be used to show that the TSOPC signal is observable through live rabbit ear but that the reconstruction does deteriorate in time (FIG. 3(c)). Remarkably, FIG. 3(c) shows that the deterioration occurred at a relatively slow rate; the measured time constant was ~1.5 seconds. This suggests that there exist volumes within the tissue for which scatterer movements are sufficiently slow and modest that optical paths through those regions are adequately stable over short periods of time. This slow deterioration rate is another good indicator that the TSOPC effect can be adapted for practical biomedical applications as the measured time constant is well within the response time of various optical technologies.

Intuitively, one may expect that the quality of the TSOPC reconstruction, as defined by the fineness of the optical field features that can be reconstructed, should drop as a function of increasing tissue turbidity or thickness. Yet, experiments have shown that the reconstruction quality remains unchanged for a broad range of tissue thickness. This surprising result had previously been predicted in published theoretical work by other groups working with simplistic scattering screens [28]. This effect can be explained by the fact that the combination of OPC playback and scattering medium works well in preserving a broad range of the original light field's spatial frequency information. This finding has significant implications as it indicates that the TSOPC effect can potentially be used to focus light with previously unachievable tightness within biological tissues. This ability can be used for novel optical therapeutic or deep tissue imaging methods with excellent resolution.

FIG. 3(d) illustrates that increased sample scattering does not have a significant impact on the TSOPC reconstruction resolution, as evidenced by the visibility of the light spot through the tissue in all three cases as scattering is increased.

At this point, it is worth noting that this TSOPC effect could have been uncovered a couple of decades ago. However, this research path was largely ignored because researchers likely figured that the high degree of scattering associated with tissues and the apparent stringent nature of such a reversal process would prevent any useful or practical TSOPC reconstruction.

Figure 3:
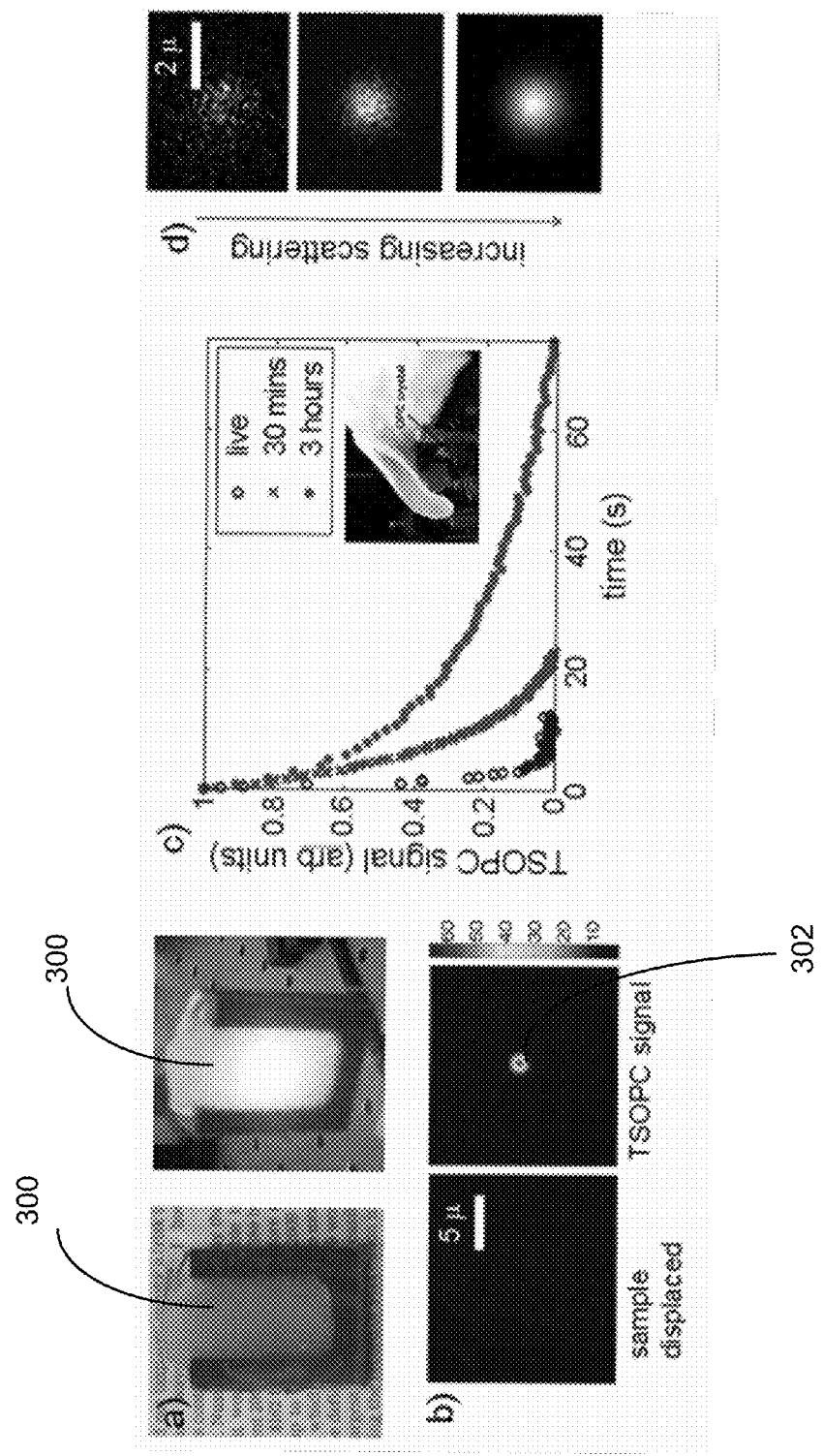
FIG. 3(a) illustrates a 7 mm thick chicken tissue section.
FIG. 3(b) illustrates TSOPC reconstruction of a light spot through the tissue section.
FIG. 3(c) illustrates a TSOPC signal is observable through live rabbit ear, wherein the decay rate of TSOPC reconstruction has a time constant of 1.5 s (live), 7.5 s (30 minutes post-death) and 32 s (3 hours post-death), and FIG. 3 (d) illustrates increased sample scattering does not have a significant impact on the TSOPC reconstruction resolution, according to one or more embodiments of the present invention.

Thus, the decay rate of TSOPC reconstruction in the sample FIG. 3 has a time constant of 1.5 s (live), 7.5 s (30 minutes post-death) and 32 s (3 hours post-death). Increased sample scattering does not have a significant impact on the TSOPC reconstruction resolution.

One may not that embodiments of the invention are fundamentally different from earlier biophotonics research into the use of holography to select unscattered light transmissions for imaging purposes [29]. Prior art methodologies may use wavefront shaping to enhance light transmission through scattering media [30]. However, the present approach is intrinsically faster and more robust, and has been shown to work with living tissues while those other researches are still progressing with simpler and mostly inorganic samples. Other prior art such as M. Fink's work [31] on RF and acoustic time-reversal, has shown that the time-reversal acoustic approach can be useful for delivering highly localized acoustic power to break up kidney stones.

It is also worth noting that the TSOPC effect suppresses scattering without resorting to any physical or biochemical modification of the tissue content. This effect can be generated at any arbitrary light intensity level. Such properties can imply that the appropriate adaption of the TSOPC effect for biomedical applications is unlikely to run into unintended phototoxicity issues. In addition, one may note that the TSOPC effect does not turn tissue transparent in the literal sense. Nevertheless, the combination of TSOPC with other optical techniques can provide the present invention with the ability to image deeper into tissue sections in a microscopy setting.

Adapting the TSOPC effect for applications does require the present invention to move away from traditional optical phase conjugation approaches. Methods based on holographic plates and photorefractive crystals are generally slow and the usable wavelength choices are largely constrained by the materials' properties. Nonlinear approaches such as four-wave mixing are fast, but they are complicated and difficult to implement and use.

Digital Optical Phase Conjugation (DOPC)

Embodiments of the present invention provide an electronic OPC approach that is flexible and easy to use. This system 400, illustrated in FIG. 4(a)-(b), combines an optical wavefront sensing system (a system for measuring the phase and amplitude variations of an incident light field that includes a wavefront sensing device 402 such as a CCD) with a spatial light modulator 404 (a reflective optical system that can alter the wavefront of the reflection). The wavefront sensing device 402 electronically records the scattered light field 406 amplitude and phase distribution. Subsequently, the data (amplitude and phase distribution data) is then electronically modified (e.g., using a computer 408) and inputted into the spatial light modulator 404 to render an appropriate optical phase conjugation light field 410.

This system 400 is capable of recording and playing back an OPC field with 768×1024 effective pixels. The system can work with any wavelength (as long as the sensor is sensitive to the wavelength), is reasonably fast (refresh rate=0.5 seconds) and is capable of generating an OPC field 410 that is actually stronger than the original scattered field input 406. This last capability is enabled by the fact that a 'blank' light field or reference beam 412 can be introduced to the system to be converted in an appropriate OPC field copy 410. Embodiments of the present invention refer to this system 400 as the digital optical phase conjugation system (DOPC), because of its optoelectronic nature.

Design of the DOPC

To generate phase conjugate wave digitally, one simply needs a device that can be used both as a sensor and as an actuator. The piezo transducer employed in acoustic time reversal experiments is a good example [37,38]. Unfortunately, such a device does not currently exist for optical processing. One can implement an equivalent system by combining a wavefront measurement device (sensor 402) with a spatial light modulator (SLM, actuator 404) in the optical arrangement as shown in FIG. 4(a)-(b).

Such a composite system works if the two components 402, 404 are exactly aligned with respect to each other so that each device 402, 404 forms a virtual image on the other device. In other words, embodiments of the present invention may provide that every pixel of the sensor 402 forms a virtual image on a corresponding pixel of the actuator 404, and vice versa.

Figure 4:
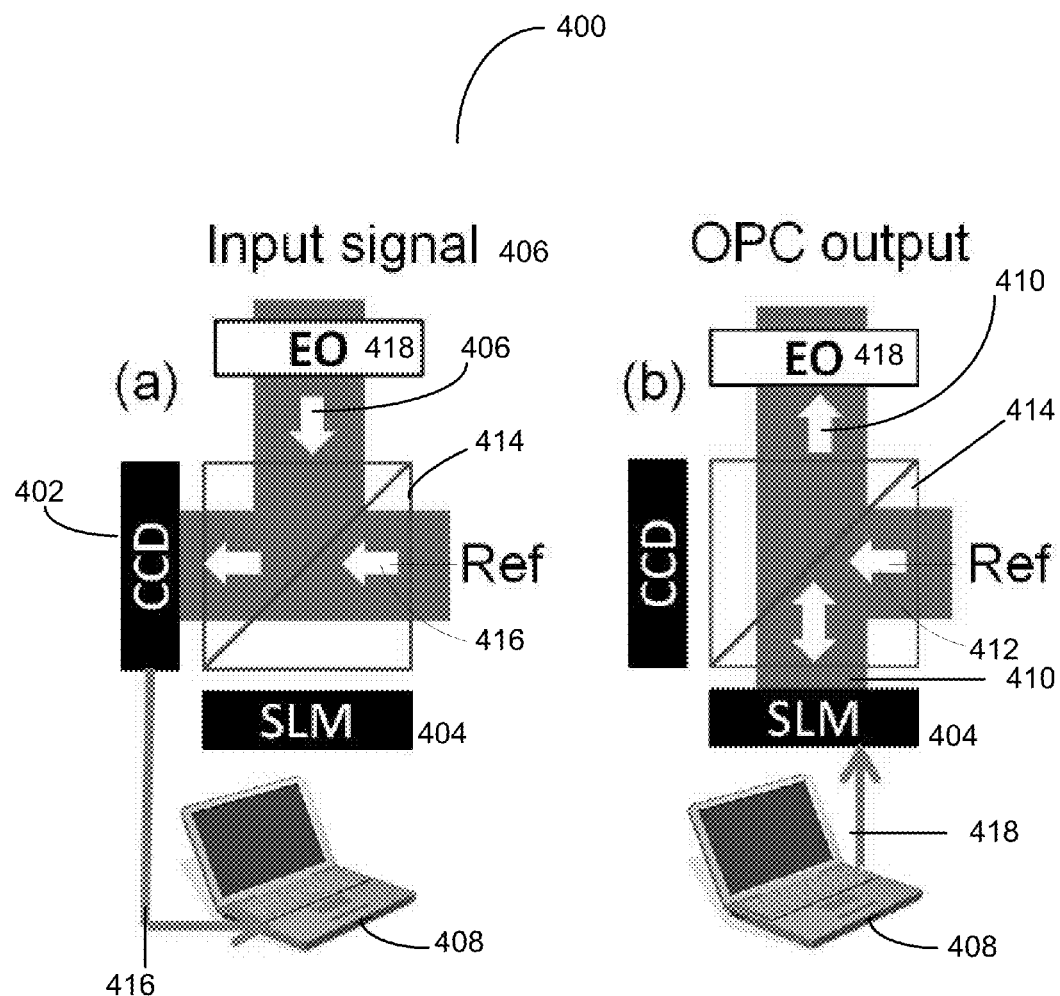

FIG. 4(a)-(b) illustrate the design of the DOPC system may further comprise a 50:50 beam splitter 414 employed to form virtual images between a CCD camera (used as the sensor 402) and a SLM 404. The generation of an OPC wave 410 then takes place in two steps. In step 1, the beam splitter 414 directs the input signal 406 towards the CCD camera 402. A reference wave 416 with a flat wavefront is provided to interfere with the unknown input wave 406 and form a hologram on the CCD 402. The relative phase between the input 406 and the reference 416 is controlled by an electro-optic (EO)

modulator 418. By using phase-shifting holography [39,40], embodiments of the present invention can uniquely determine the phase and amplitude information of the input wave 406. In step 2, the measured wavefront is digitally reversed by a computer 408 and passed to the SLM 404. The reflection 410 of the reference beam 416 incident on the SLM 404 is modulated and counter-propagates with respect to the input wave 406, and the reflection 410 is the phase conjugate of the input signal 406. Thus the computer 408 is connected to the CCD 402 to receive 416 the amplitude and phase information of the input wave 406 and output 418 information, to the SLM, wherein the information is used for positioning the SLM pixels to create the optical phase conjugate of the input wave.

The advantages of the DOPC system may include: (1) the same system can be used for both CW and pulsed lasers; (2) the DOPC system can work flexibly at any wavelength and at any light intensity; (3) the power of the generated OPC wave is independent of the input signal and can be precisely controlled by a computer. With such a system, the OPC reflectivity, defined by the power ratio of the OPC signal to the input signal, can be freely controlled; (4) the operation of the DOPC system is open loop, requiring no iterative measurements or computations; (5) the large number of digitally controlled degrees of freedom allows for the flexible alteration of the OPC wavefront. This last property may be useful in studying the interaction of the OPC wave with the turbid medium.

Experimental Set Up

This section describes an experimental implementation of the DOPC system and its required calibration procedure, that ensures an accurate mapping between the measured wavefront and the SLM output in accordance with one or more embodiments of the invention.

Figure 5:
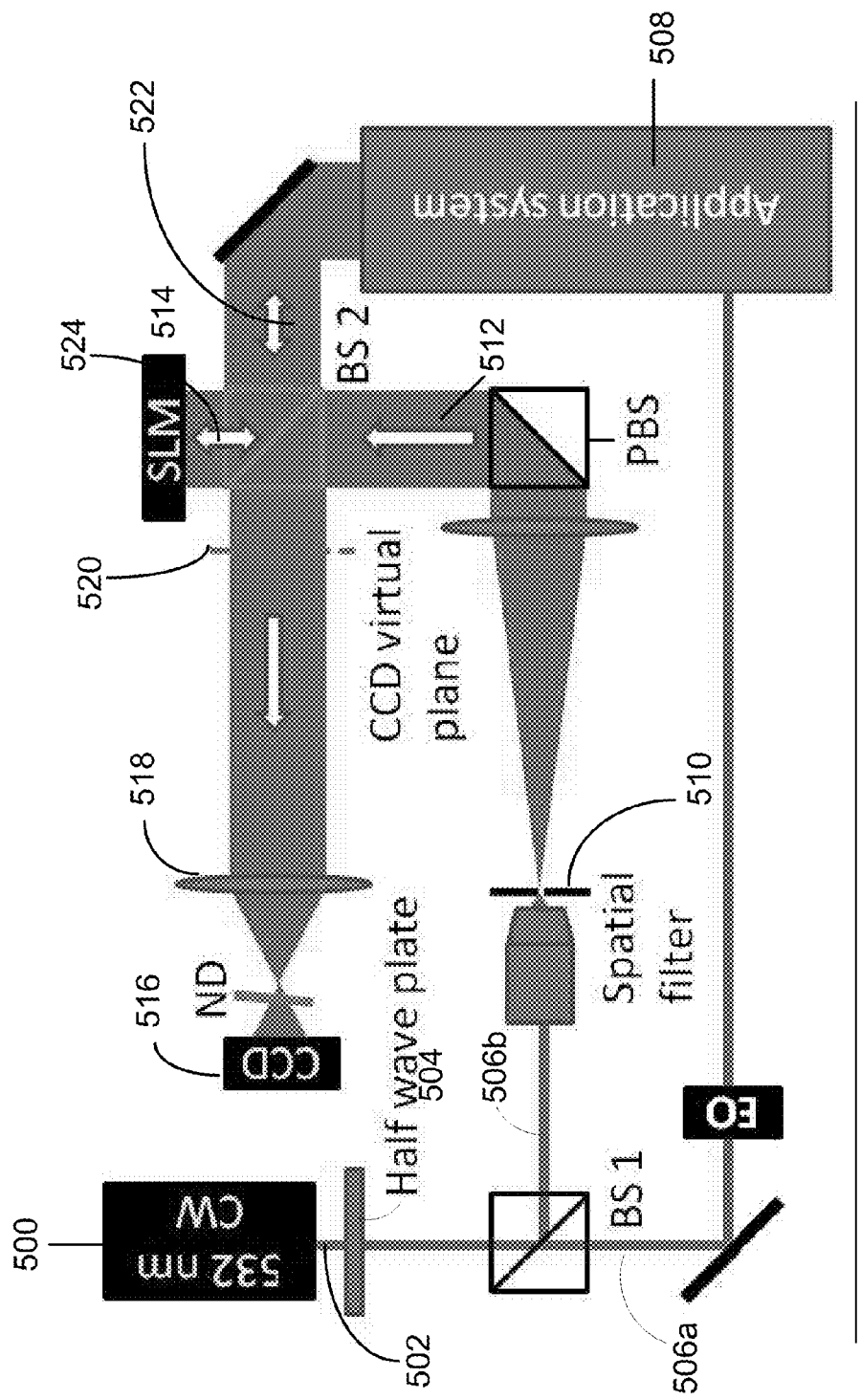
FIG. 5 illustrates an experimental setup of the DOPC system, according to one or more embodiments of the present invention, comprising a solid state CW (continuous wave) laser at 532 nm (e.g., a Spectra-Physics, Excelsior Scientific 200 mW), an SLM that is a LCOS reflective spatial light modulator (e.g., a Holoeye, LC-R 2500), a CCD that is a CCD camera (e.g., an ImagingSource DFK41BF02), a polarizing beam splitter (PBS), beam splitters BS1 and BS 2, non-polarizing beam splitter, and a neutral density filter (ND)

FIG. 5 shows an experimental setup of the DOPC system. A solid state continuous wave (CW) laser 500 emitting at 532 nm wavelength (e.g., a Spectra-Physics, Excelsior Scientific 200 mW) was employed in the experiment. Its output 502 first travels through a half wave plate 504 and is split to two beams 506a and 506b by a non-polarizing beam splitter (labeled BS 1 in FIG. 5). One beam 506a travels through an EO phase modulator (labeled EO in FIG. 5) and enters the application system 508 (e.g., comprising the turbid medium or sample). The other beam 506b is spatially filtered in a spatial filter 510 and is used as the reference beam 512 of the DOPC system. The reference beam 512 is directed by a polarizing beam splitter (labeled PBS in FIG. 5) towards a non-polarizing beam splitter (labeled BS 2 in FIG. 5) placed in front of a SLM 514 (768×1024 pixels). Ideally, BS 2 can be placed at the symmetry plane between the SLM 514 and the CCD 516 and the SLM 514 should form a mirror image onto the CCD 516, and vice versa. In practice, the size of the CCD 516 pixel size can be smaller than the SLM 514 pixel size and a lens 518 can be used to form an enlarged image of the CCD 516 at the symmetric position as shown by the "CCD virtual plane" 520 in FIG. 5. Also shown in FIG. 5 is a neutral density filter, labeled ND.

The SLM 514 is mounted on a tilt and rotation platform driven by two differential micrometers (e.g., Newport, DM-13).

The input signal 522 (that is provided by the application system 508 from signal 506a) enters the DOPC system from the right side of BS 2 and interferes with the reference beam 512 to form a hologram on the CCD 516. The relative phase between the signal beam 522 and the reference beam 512 is modulated by the EO modulator. At the end of the phase-shifting holography, the phase information is retrieved by the computer from the holograms and passed to the SLM 514 that outputs the phase conjugate signal 524, a wave that counter-propagates with respect to the input signal 522 with a reversed spatial phase profile. The power of the phase conjugate wave 524 is determined by the power of the reference beam 512 and is independent from the input signal 522, allowing one to arbitrarily control the phase conjugation reflectivity. The input wave 522 also entered the SLM 514 and the input wave's 522 reflection from the SLM 514 becomes a part of the output wave 524.

Thus, supposing the input signal 522 is given by $E(x,y)\exp(i\phi(x,y))$, with the reversed phase profile $-\phi(x,y)$ displayed on the SLM 514, the reflected input signal by the SLM 514 becomes $E(x,y)\exp(i\phi(x,y)-i\phi(x,y))=E(x,y)$ that is a wave with a flat spatial phase profile, just as the reference wave 512. Experimentally, this signal may be much weaker than the correctly shaped DOPC output 524.

During the wavefront measurement, a portion of the reference beam 512 is reflected by the SLM 514 and enters the application system 508. As long as the application system 508 is not highly reflecting, this reflection does not significantly impact the wavefront measurement since this reflection is not phase modulated by the EO modulator. During the phase shaping, a portion of the reference beam 512 is directed towards the CCD 516 detector. The ND filter may be oriented in front of the CCD 516 such that the reflected light does not enter BS 2.

Calibration

The proper operation of the DOPC system requires that the CCD and SLM are correctly oriented with respect to each other, and that the phase measured by the CCD is appropriately mapped to the SLM. Since the reflection light field from the SLM does not actually fall on the CCD in the DOPC design, the alignment of the two elements cannot be trivially done. Instead, embodiments of the present invention have developed an alignment protocol that employs a sieve-like mask to serve as a referencing system during alignment. this protocol is described below.

One first ensures that the SLM is perpendicular to the incident reference beam. To align the SLM, the light that back-propagates through the spatial filter 510 and BS 1 in FIG. 5 is measured, and the back-propagating signal is maximized by adjusting the tilt and rotation platform carefully.

The more challenging calibration step is the correct mapping of the wavefront measurement at the CCD to the SLM output. A three-step procedure may be employed to address this issue. A chrome mask 600 with 10 micron diameter holes 602 and 20 micron hole spacing was made for the calibration.

Figure 6:
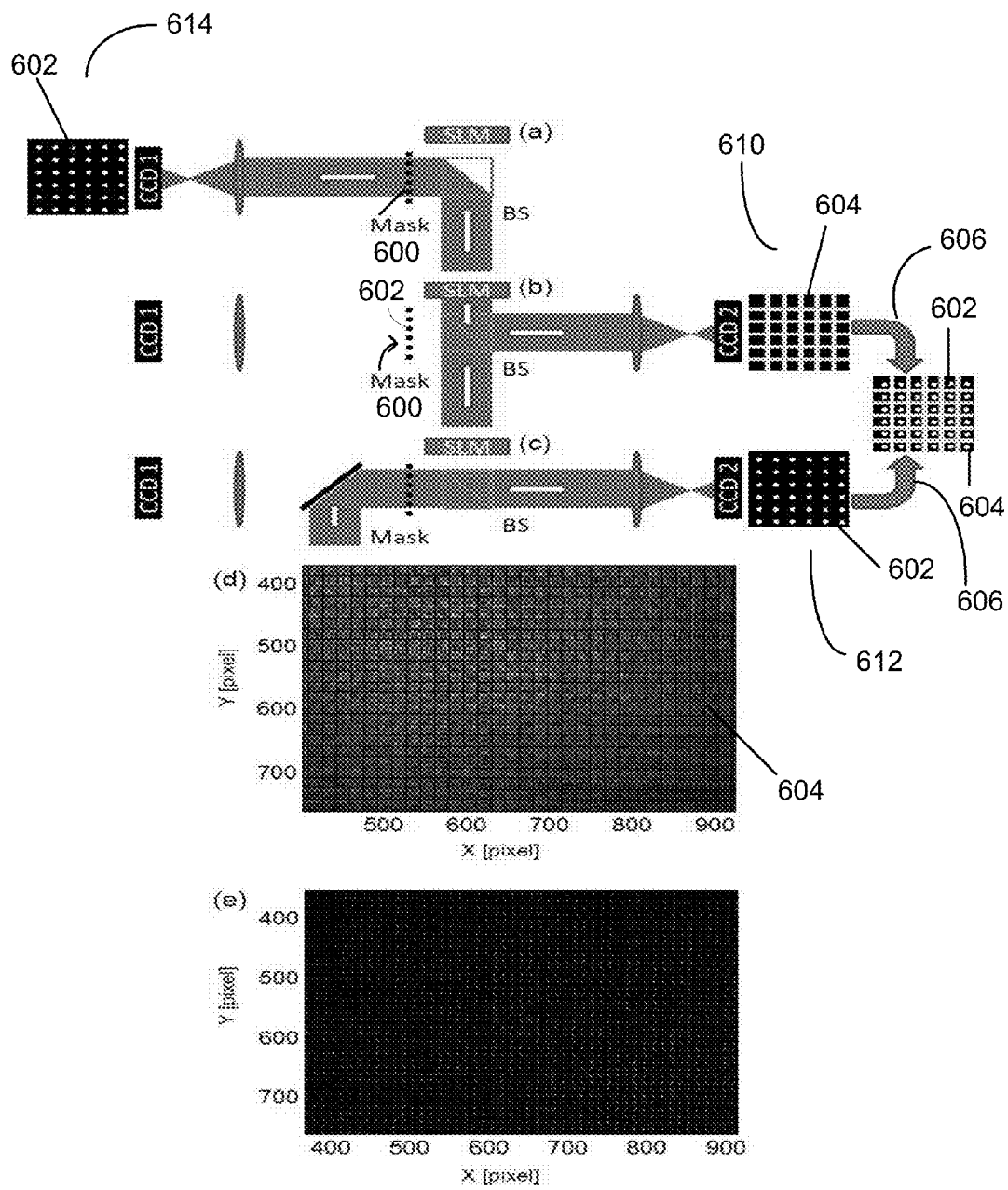
FIG. 6 illustrates a procedure for mapping between the CCD and the SLM, according to one or more embodiments of the present invention, wherein FIG. 6 (a) shows a mask that was placed at the symmetry plane of the SLM and illuminated and imaged on CCD 1.

In step 1, the mask 600 is placed at the symmetry plane of the SLM as shown in FIG. 6(a). The reflective mask and the SLM form a Michelson interferometer. The phase of the SLM is set to 0 and the orientation of the mask is adjusted while observing the interference pattern formed by the SLM and the mask. In such a way, one can make sure that the mask is parallel to the symmetry plane. The mask is mounted on a translation stage. The distances from the SLM and the mask to the beam splitter BS are measured to ensure that their difference is less than 0.5 mm. Since the SLM pixel size is ~20 micron and the Rayleigh range of a 532 nm Gaussian beam with 10 micron beam waist is greater than 1 mm, a difference less than 0.5 mm is accurate enough for the purpose of calibration. The mask is illuminated and the transmitted light is imaged onto CCD 1 which is the CCD camera used in the DOPC experiment.

In step 2, the SLM is illuminated and the transmitted light is imaged onto another camera (CCD 2), as shown in FIG. 6(b). The SLM is divided into 64×48 blocks with 16×16 pixels 604 in each block. The phase differences between adjacent blocks were set to π. Such an abrupt phase variation may cause scattering. If the scattered light is not completely collected by the imaging system, the edges of the phase blocks may appear dark in the image. In such a way, phase shaping may be used to produce an intensity pattern on the acquired SLM image. FIG. 6(d) is an image of the SLM and the SLM pixels 604 experimentally acquired in step 2.

In step 3, the mask is illuminated and the transmitted light is imaged onto CCD 2, as shown in FIG. 6(c). FIG. 6(e) is an image of the mask acquired in step 3. By comparing 606 the images 610, 612 acquired in step 2 and step 3, the relative position between the SLM pixels 604 and the holes 602 on the mask 600 can be determined. The image 614 on CCD 1 acquired in step 1 provides information about the hole 602 positions on CCD 1. In such a way, one can map the SLM pixels 604 onto CCD 1.

Experimental Test

Performance of the DOPC system can be evaluated by examining its ability to accurately measure the light field from a point source and generate the phase conjugate field that can refocus at the point source.

Figure 7:
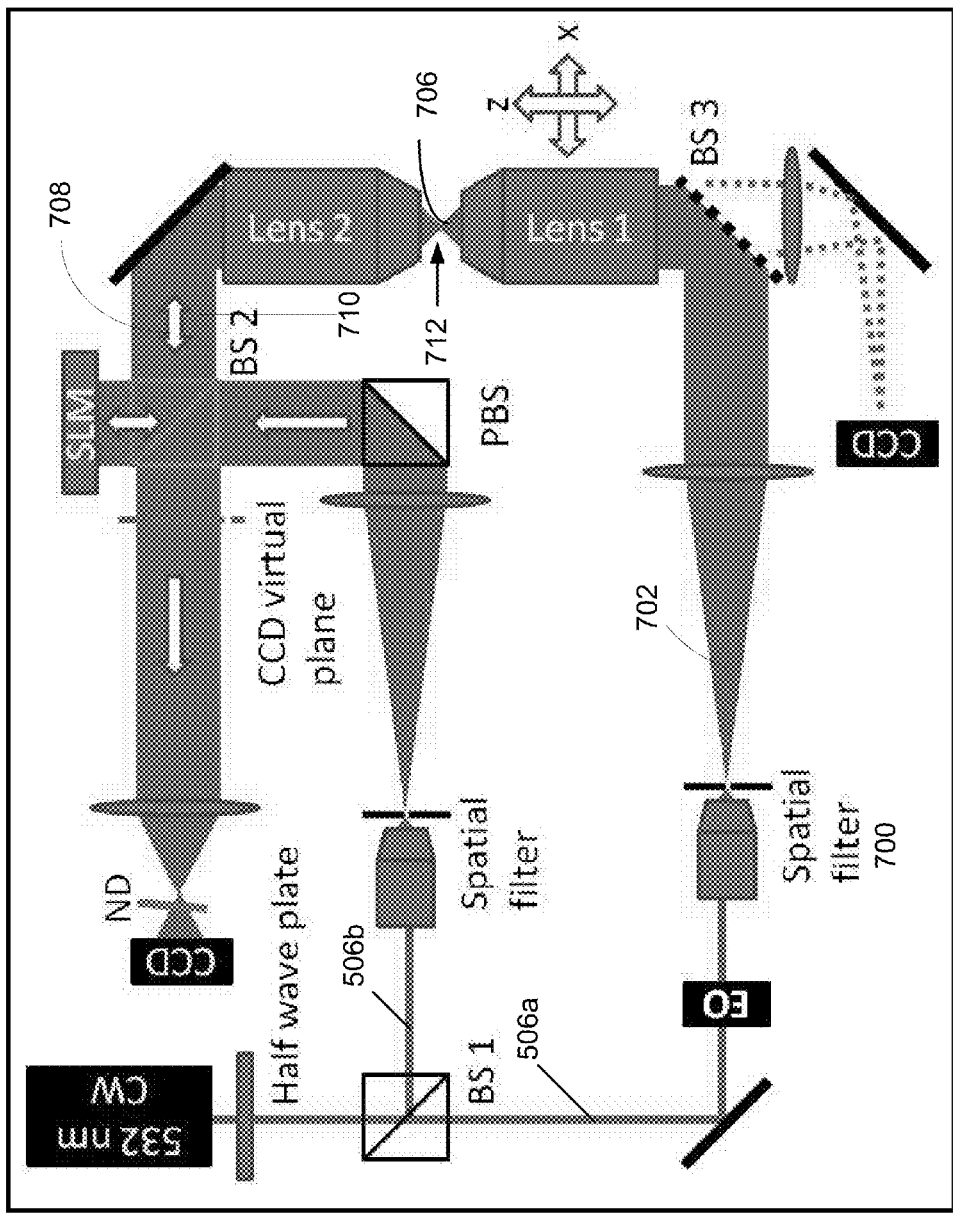
FIG. 7 illustrates a setup for testing the accuracy of DOPC, according to one or more embodiments of the present invention, comprising a solid state CW laser at 532 nm, a SLM that is a LCOS reflective spatial light modulator (e.g., a Holoeye, LC-R 2500); a CCD camera (e.g., an ImagingSource DFK41BF02), a PBS, a beamsplitter BS, a non-polarizing beam splitter, an electro-optic phase modulator (EO) (e.g., a Thorlabs, EO-PM-NR-C4), objective lenses Lens 1 and 2 (e.g., an Olympus, UPLFLN 100XO2, NA1.3), and a neutral density filter (ND)

The experimental setup is shown in FIG. 7. To create a point source whose position can be controlled, beam 506a is sent through a spatial filter 700 and the resulting spatially filtered beam 702 is sent through a numerical aperture (NA)=1.3 oil immersion objective lens (Lens 1 in FIG. 7) that was mounted a translation stage 704 driven by differential micrometers (e.g., Newport, DM-13). The focused beam 706 is collected by another identical objective lens (Lens 2) and directed to the DOPC system. The generated phase conjugate beam 708 counter-propagates with respect to the input signal 710 through Lens 2 and is refocused at the point source 712. To measure the position accuracy and stability of the DOPC generated focus 712, a beam splitter (BS 3 in FIG. 7) may be placed near the back aperture of Lens 1, the transmitted phase conjugate beam 708 is directed towards a lens, and the beam is focused on a CCD detector 714.

Figure 8:
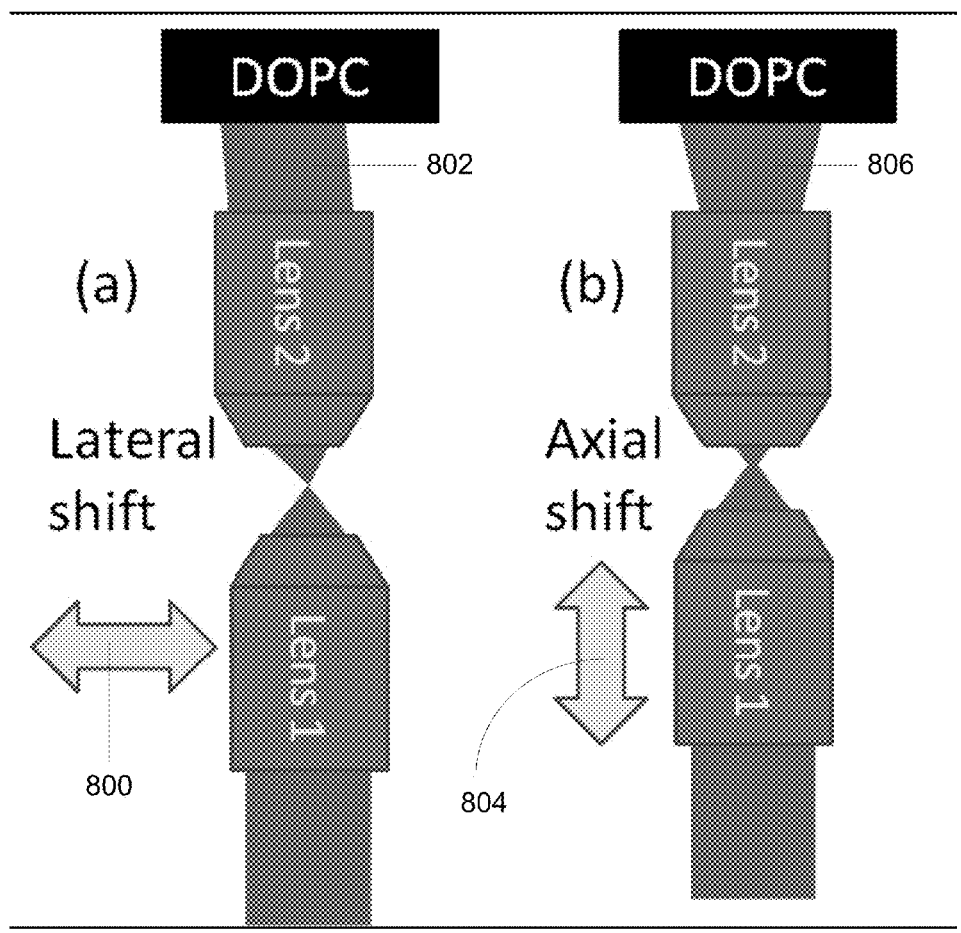
FIG. 8(a) illustrates that as Lens 1 was shifted in the lateral direction, the beam exiting Lens 2 deviated from the original propagation direction, and FIG. 8 (b) illustrates that as Lens 1 was shifted in the axial direction, the beam incident on the DOPC system was either a converging or a diverging beam, according to one or more embodiments of the present invention.

In the first test, Lens 1 is translated in the lateral direction 800, as shown in FIG. 8(a). In such a case, the beam 802 exiting Lens 2 deviated from its original propagation direction. In the second test, Lens 1 is translated in the axial direction 804, as shown in FIG. 8(b). In such a case, the beam 806 exiting Lens 2 became either a diverging or a converging beam.

Figure 9:
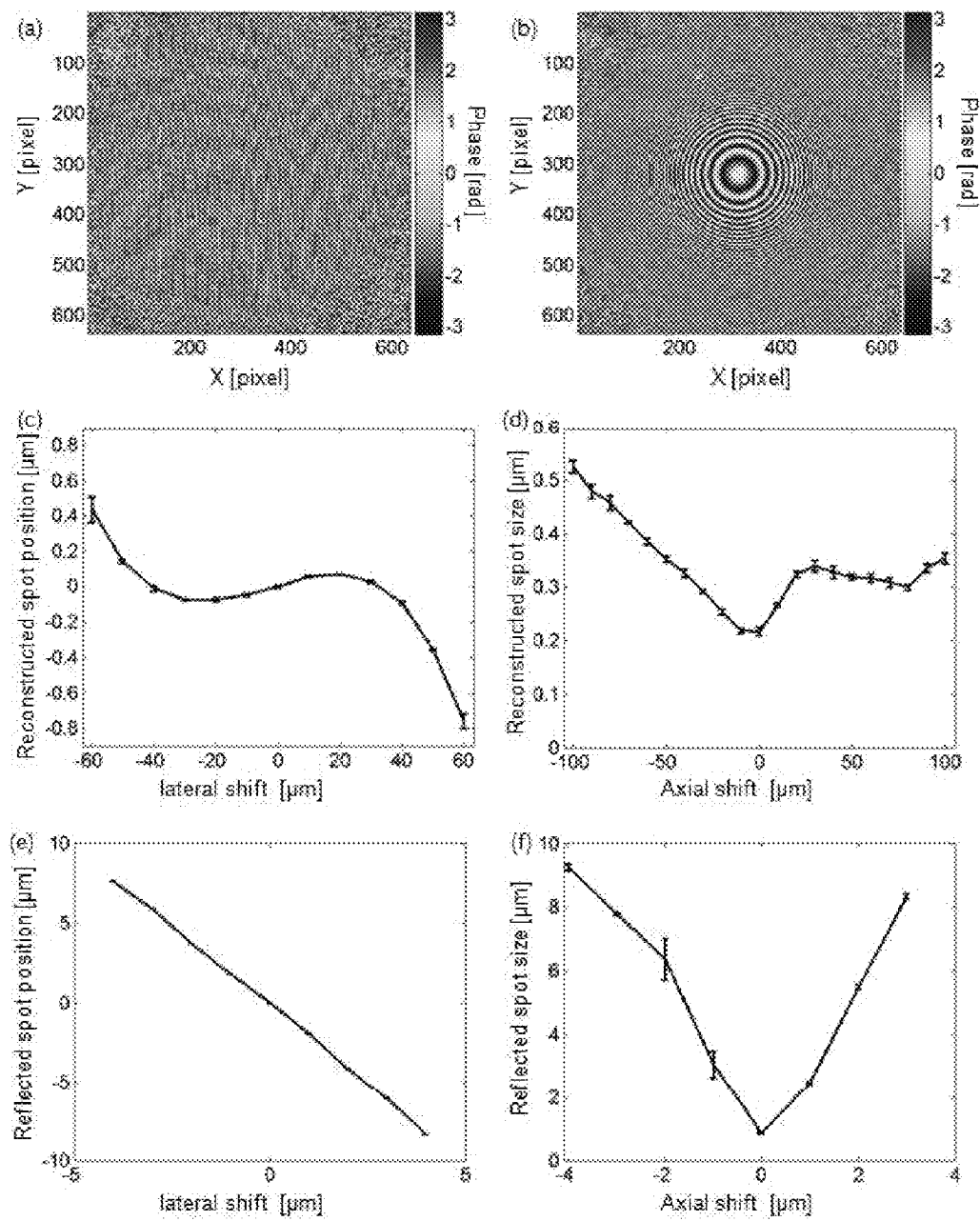
FIG. 9(a) illustrates the phase shifting holography measured wavefront when lens 1 was shifted laterally from the center position by 50 microns.
FIG. 9(b) illustrates the measured wavefront when Lens 1 was shifted axially from the center position by 50 microns, FIG. 9 (c) illustrates the DOPC reconstructed focus position as Lens 1 was shifted laterally.
FIG. 9(d) illustrates the DOPC reconstructed focus diameter as Lens 1 was shifted axially, FIG. 9 (e) illustrates the measured reflected focus position variation when Lens 1 was shifted laterally.
FIG. 9(f) illustrates the reflected focus size variation when Lens 1 was shifted axially, according to one or more embodiments of the present invention.

The experimental results of the experiment of FIGS. 7 and 8(a)-(b) are summarized in FIGS. 9(a) and 9(b). FIGS. 9(a) and 9(b) are the wavefronts measured by phase-shifting holography when Lens 1 was shifted by 50 microns laterally (a) and axially (b) from the centered position.

The lateral displacement of Lens 1 caused the beam entering the DOPC system to deviate from the normal incidence angle on the SLM. Consequently, the measured phase had a constant slope in the lateral direction. Fourier analysis showed that there were ~2.5 pixels per 2π phase variation in FIG. 9(a).

The axial displacement caused the beam entering the DOPC system to become either a converging beam or a diverging beam such that the phase slope gradually increased from the center to the outer area.

FIG. 9(c) shows the reconstructed focus position as Lens 1 was shifted from −60 to 60 microns. From −50 to 50 microns, the standard deviation from the center position is ~0.12 micron, which is small compared to the 0.23 micron focus diameter.

FIG. 9(d) shows the reconstructed focus size as Lens 1 was shifted axially from −100 to 100 microns. The spot size variation is asymmetric. In the case of negative axial displacement, the beam exiting Lens 2 was a diverging beam that could fill the entire SLM. The phase variation near the center was slow and could be accurately sampled and compensated by the DOPC system. The phase variation near the outer area of the SLM could exceed the sampling rate of the DOPC system and cause error. In the case of positive axial displacement, the beam exiting Lens 2 was a converging beam that could only fill the center area of the SLM. The high spatial frequency components were truncated by the objective lens, which caused the asymmetry in FIG. 9(d).

As a comparison, a mirror may replace the DOPC system in FIG. 7 and used to perform the lateral and axial displacement experiments. FIG. 9(e) shows the lateral displacement results. Linear fitting shows a slope of 1.99, which is expected since the angle deviation doubled upon reflection by the mirror. FIG. 9(f) shows the axial displacement result. Without DOPC compensation, one micron displacement caused the reflected spot size to increase by more than tenfold to ~3 micron.

Compensation Range of the DOPC System

The optical degrees of freedom of the DOPC system are limited by the pixel numbers of the SLM and the CCD camera. Given the number of pixels, embodiments of the present invention can estimate the amount of lateral displacement that can be compensated by the DOPC system. The SLM employed in various experiments has 768×1024 pixels that were mirrored onto an area on the CCD camera which contains slightly more pixels. In the experiments, 634×634 SLM pixels were imaged to the back aperture (~5 mm in diameter) of the 100× objective lens. The maximum phase difference between adjacent pixels is π (Nyquist frequency), such that the total phase variation across the 634 pixels is $634\pi$ ($317\lambda$). The maximum angle deviation that can be compensated is therefore $317\lambda/5$ mm and the maximum lateral deviation at the focal plane is then $317\lambda f/5$ mm, where f is the focal length of the objective. For an Olympus 100× objective, the focal length is ~1.8 mm and the theoretical maximum deviation from the center is therefore ~61 micron ($\lambda$=532 nm). The experimentally achieved lateral compensation range in our system is ~50 micron.

Evaluation with a Random Scattering Medium

A potential application of DOPC is to reconstruct an optical mode through a highly turbid medium. To demonstrate such a capability, and as a stringent test, one can apply the DOPC system to return an OPC wave through a scattering medium of $\mu_s l$ ~13.

Embodiments of the invention employed the setup shown in FIG. 7 for the demonstration. To prepare a random scattering sample, a mixture of polystyrene microspheres of different diameters (0.2, 0.5, 1, 3, 5, 10 μm) with equal weight percentage is dried in a water suspension on a cover glass.

Immersion oil is added on top of the microspheres and covered with another cover glass. The quantity of $\mu_s l$ can be determined by measuring the transmitted ballistic light. Experimentally, a collimated laser beam 1 mm in diameter can be used to illuminate the sample. The transmitted light was directed through an iris 1 mm in diameter placed 3 meter away from the sample, and was measured with a power meter (e.g., a Newport 1830). To avoid overestimation of $\mu_s l$ due to refraction, a mirror may be used to slightly adjust the propagation direction of the transmitted light to ensure that the ballistic component enters the iris. Through the ballistic light measurement, a $\mu_s l$ of ~13 was determined.

The scattering sample was mounted on a translation stage and inserted between the two objectives Lens 1 and Lens 2 in FIG. 7). The experiments were performed in three steps. In step 1, the wavefront of the beam propagating through Lens 1, the sample, and Lens 2 was measured. In step 2, the DOPC system was enabled by displaying the correct phase profile on the SLM. In such a case, the DOPC output should retrace the scattering path through the sample and become a collimated beam. In step 3, the DOPC system was disabled by setting the phase of the SLM to 0 (no phase modulation) and the transmission of the disabled DOPC output through the sample was measured. One would expect to observe a random scattering pattern since the beam entering Lens 2 is approximately a plane wave.

Figure 10:
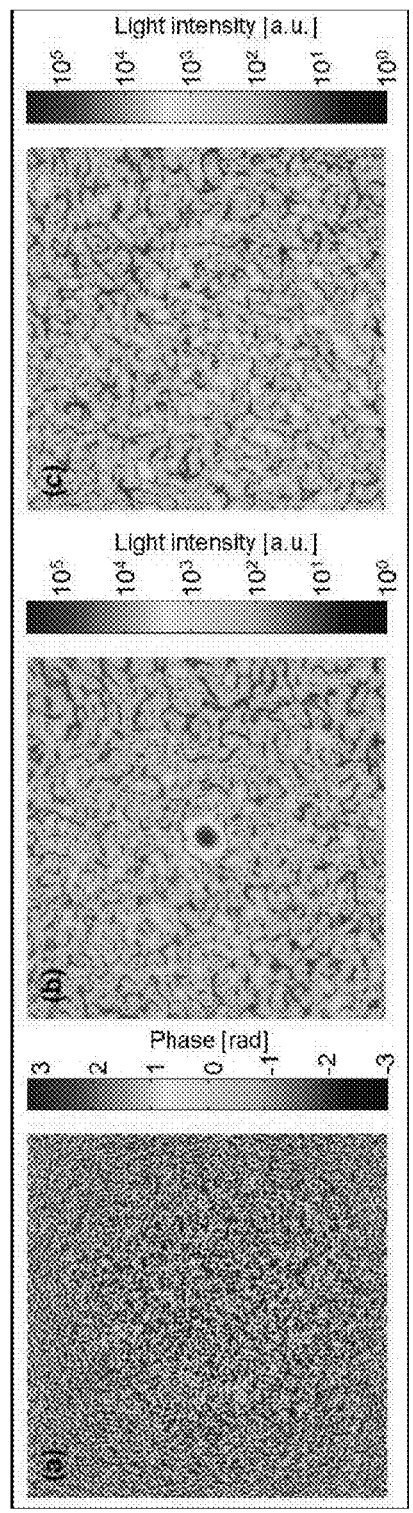
FIG. 10 (a) illustrates the DOPC measured phase profile.

FIG. 10(*a*) is the measured wavefront of the beam propagating from Lens 1 to Lens 2. The random scattering inside the sample severely distorted the spatial phase profile. FIG. 10(*b*) shows the transmission of the enabled DOPC output. In such a case, the phase conjugate wave retraced its way through the scattering medium and became a collimated beam. The Full Width at Half Maximum (FWHM) of the reconstructed signal is ~0.43 micron, that is, greater than the diffraction limited resolution (0.23 micron). FIG. 10(*c*) shows the transmission of the disabled DOPC output through the sample. Since the disabled DOPC output is approximately a plane wave that is not matched to the phase profile of the sample, the transmission displays a random scattering pattern. The measured peak to background ratio in FIG. 10(*b*) is ~600. According to Ref [3,25], the peak to background ratio is a direct measure of the optical degrees of freedom. The number of independent optical modes was estimated from the measured phase profile [FIG. 10(*a*)] to be ~1000, which is reasonably in agreement with the measured peak to background ratio.

The Impact of Phase Error on the Process of Optical Phase Conjugation Through a Random Scattering Medium One can reasonably expect that the effectiveness of OPC through a scattering medium to reconstruct an initial input field should depend on the accuracy by which the phase conjugate field is produced. The exact relationship between fidelity and reconstruction efficiency is important and relevant as it can provide a guide in making informed design choices in OPC-based applications. However, this relationship is difficult to study experimentally with conventional OPC methods as it is difficult to controllably introduce errors into the phase conjugate fields.

The DOPC system affords us an easy and well controllable means for introducing known phase errors into the OPC wavefront. The desired phase shifts are simply added into the DOPC wavefront that the SLM generates.

This section presents a theoretical analysis and experimental verification of the deterioration of the OPC reconstruction signal through a scattering medium when phase errors are present in the OPC wavefront.

The scenario is as follows. Consider an initial single optical mode incident on a random scattering medium. Suppose the medium is of sufficient thickness so that the transmitted light is composed of a large number of uncorrelated optical modes. If the phase profile of this transmitted field is recorded and returns an OPC field that has a phase profile of opposite sign, one can expect to obtain an optimal reconstruction OPC signal when the OPC field is retransmitted through the scattering medium. If, instead, random phase errors are introduced into the OPC wavefront, one can expect the reconstructed OPC signal to diminish in strength. This section aims to address the exact deterioration relationship.

More formally, the scenario described above can be expressed mathematically as follows. The transmission of an optical wave through random scattering media can be described with a transmission matrix t [3]. Suppose a single optical mode $E_a|a\rangle$ is incident on a random scattering medium, where $E_a$ is the complex amplitude of mode $|a\rangle$. Its transmission can be described by $$\sum_b E_a t_{ba} | b \rangle$$

where $|b\rangle$ represents a transmitted free propagating mode. Its phase conjugation is therefore $$\sum_b E_a^* t_{ba}^* | b \rangle.$$

If the phase conjunction wave propagates back through the scattering medium, the complex amplitude of the reconstructed mode $|a\rangle$ becomes $$E_a' = \sum_b E_a^* t_{ba}^* t_{ab}.$$

Due to reciprocity, $t_{ab}=t_{ba}$ and hence $$E_a' = E_a^* \sum_b |t_{ba}|^2.$$

If a random phase error is present in the phase conjugation wave, the complex amplitude of the reconstructed mode $|a\rangle$ becomes $$E_a'' = E_a^* \sum_b |t_{ba}|^2 \exp(i\phi_b),$$

wherein $\phi_b$ represent a random phase error in mode $|b\rangle$. The power ratio of the imperfect OPC signal to the perfect OPC signal is therefore, $$R_{power} = \left| \frac{E_a''}{E_a'} \right|^2 = \left| \frac{\sum_b |t_{ba}|^2 \exp(i\phi_b)}{\sum_b |t_{ba}|^2} \right|^2 \quad (1)$$

Figure 11:
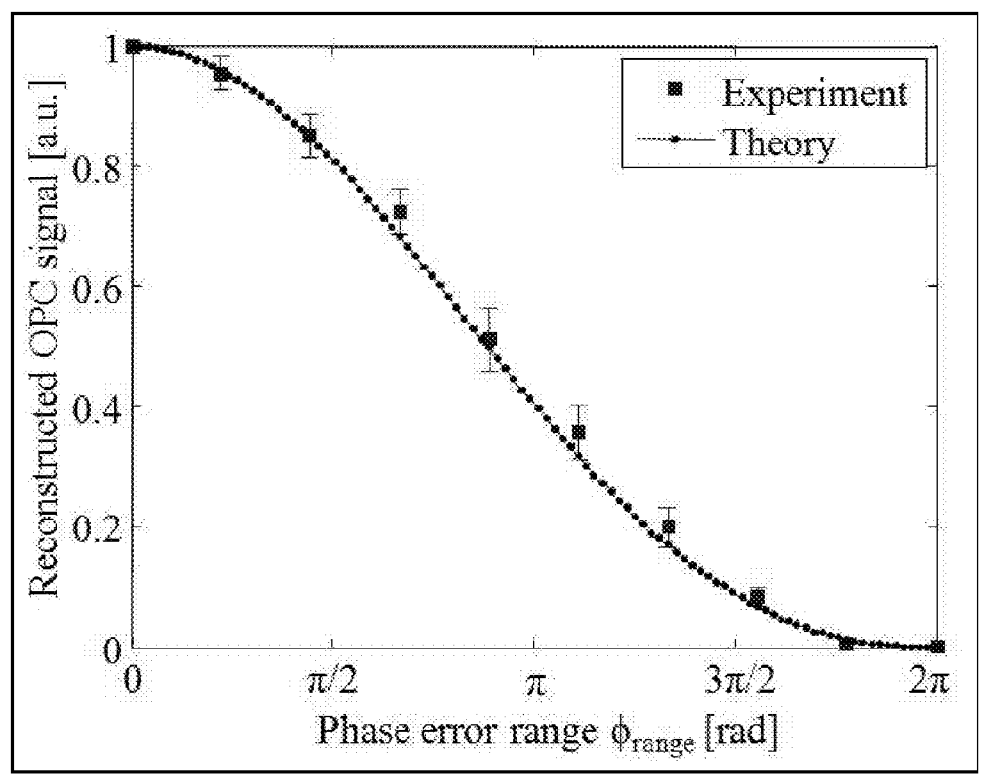
FIG. 11 is a theoretical calculation and experimental measurements of the reconstructed OPC signal dependence on the amount of phase error, according to one or more embodiments of the present invention.

To evaluate Equation (1) above, a random number is assigned to each $\phi_b$ ranging from $-\phi_{range}/2$ to $\phi_{range}/2$ (uniform probability distribution) and assumes that $|t_{ba}|^2$ obeys a negative exponential distribution, since the transmitted light through a sufficiently thick random scattering medium appears as a speckle pattern [26]. The calculated result is shown in FIG. 11 (dotted line). Surprisingly, this model predicts that the reconstructed OPC signal decreases rather slowly with increasing phase errors. Even when $\phi_{range}$ reaches $\pi$, such that the phase error is a random number between $-\pi/2$ and $\pi/2$, the reconstructed OPC signal would still be ~40% of its peak value (when no phase error is present). In the above analysis, the input signal is a single optical mode.

Using the transmission matrix theorem, the case when the input signal consists of multiple optical modes (an image) can also be examined. Numerical evaluation shows that the reconstructed image has the same dependence on phase error as shown in FIG. 11 (dotted line).

To experimentally verify the theoretical prediction, a random scattering medium with $\mu_s l \sim 10$ as the sample can be used. The experimental procedure is the same as that described above.

DOPC is performed to reconstruct the input signal and measure the strength of the reconstructed signal. Random phase errors are digitally added to each mode of the generated phase conjugate wave and the range of the phase error $\phi_{range}$ is gradually increased while observing the OPC signal peak intensity variation. The experimental results are summarized in FIG. 11 (solid squares with error bars), and agree well with the theoretical prediction.

Biochemical Sensor

Figure 12:
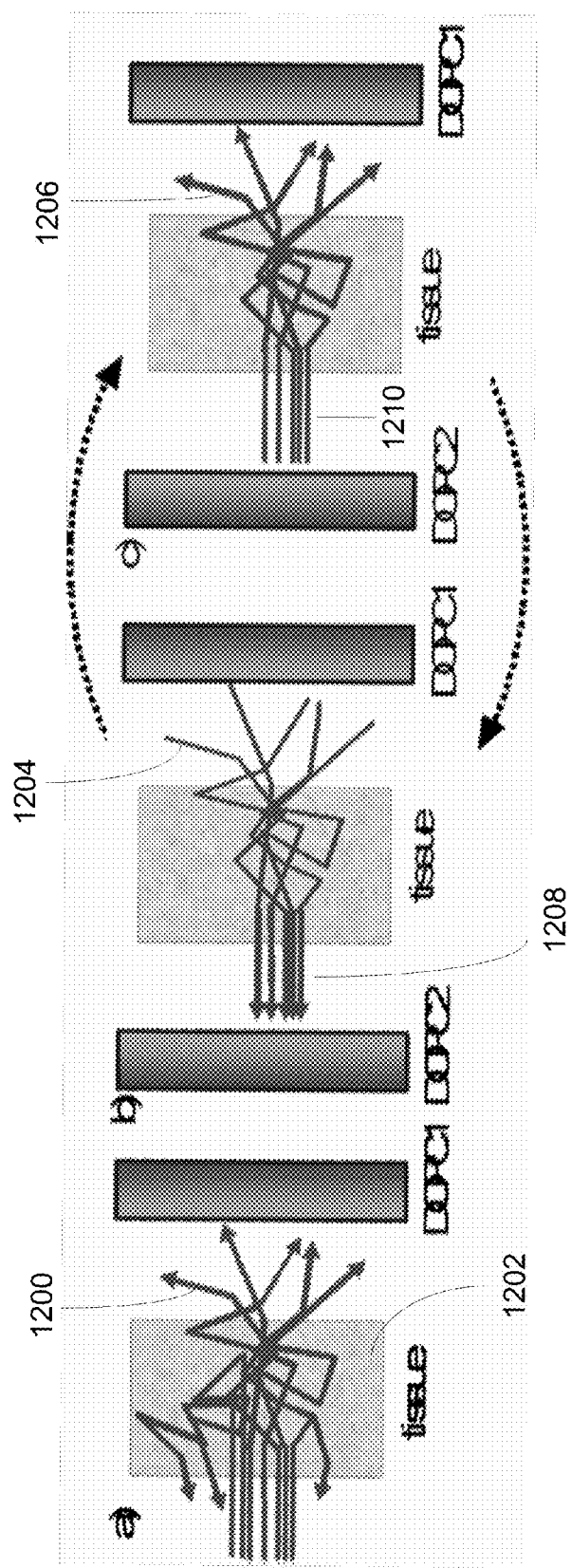

Embodiments of the invention further include a high sensitivity in-vivo biochemical sensor (see FIG. 12).

In such embodiments, a light beam 1200 of a specific wavelength is transmitted through a tissue slab 1202 and applied to a first DOPC (DOPC1) to generate an OPC field 1204 that is then returned back through the tissue slab 1202. The attenuation of that transmission process is then measured.

The present invention then uses a second DOPC (DOPC2) to return this second transmission 1204 through the tissue 1202, and measure a third transmission 1206. This process may be repeated several times.

The collected measurements may be processed to determine the absorption coefficient of the tissue at that wavelength. Roughly speaking, this process works by zeroing the impact of the scattering on light transmission through the tissue and leaving absorption as the primary determinant factor of the light transmission efficiency.

Conceptually, one may think of photons that were initially transmitted through the tissue slab as traveling within a class of 'open' channels which connect one side of the tissue with the other. Photons that are not transmitted had traveled instead through 'closed' channels. By recording the light field pattern of the transmission and projecting an OPC copy onto the tissue, photons are preferentially sent back through those 'open' channels and avoids the closed ones. This improves overall transmission of the OPC field.

Practically, this process may be iterated several times because the TSOPC playback process is not perfect. By repeating the process, results may converge on a light field profile that sends photons optimally down those 'open' channels. Mathematically, the present invention expects this ideal convergent profile to transmit light with an asymptotic value of 66% efficiency through a pure scattering medium, regardless of sample thickness and turbidity [10]. Effectively, this ideal convergent solution, also called universal optical transmission (UPT), may ignore the presence of scatterers within the sample because the photons are efficiently directed into the 'open' channels and are free to go from one side of the scattering medium to the other. The presence of absorption within the samples partially absorbs these 'open' channel photons and results in a diminished net transmission. As such, by measuring the transmission deviation from 66%, one may determine the amount of absorption within the sample. This strategy deviates from most existing absorption based biochemical sensing in that embodiments of the present invention actively suppress scattering contributions in order to simplify absorption measurements.

Applications of this method include measuring blood glucose level through the webbing between fingers by collecting absorption measurements in the near-infrared regime, and measuring the concentration of bilirubin in newborn infants (wavelength range of 450 nm to 500 nm).

Embodiments of the present invention may be used on phantoms, tissue models, animal models and humans. Tissue thickness limit, the light fluence level requirements, and the requisite system response time are all factors that may be experimentally evaluated.

The biochemical sensor is enabled by the DOPC system described herein, which allows the flexible recording and playback of light fields over a broad range of wavelengths and effective reflectivity. While it can be experimentally demonstrated that the concept of UPT can ignore scatterer presence, the construction of such a UPT for living tissues may depend on additional factors. Primarily, response time adequacy of a DOPC system may be an issue. As such, some embodiments may speed up the DOPC to operate in the 10's millisecond range.

For example, the theoretical and experimental results prove that the reconstruction of an original light field by OPC through random scattering media is robustly tolerant to phase errors. It suggests that phase accuracy may be reasonably sacrificed to improve other aspects of the experiments in many adaptive optics methods for OPC through random scattering media, such as the experiment speed. For example, to accurately modulate the phase profile over $2\pi$, many pixels are required. Findings suggest that binary phase shaping can be used to achieve a comparable level of OPC signals while greatly reducing the required pixel number and increasing the experiment speed.

However, even if the ideal UPT solution is not achieved, embodiments of the present invention may benefit from a significant turbidity suppression that makes absorption measurements easier.

Raman Spectroscopy

One or more embodiments of the present invention apply the concept of UPT to perform spontaneous Raman spectrum measurements in an in-vivo setting. The Raman emission spectra of molecules reveal a highly specific fingerprint pattern that can be used to identify and quantify the biochemical content of tissues.

In-vivo Raman measurements are confounded by the fact that tissue scattering prevents efficient and deep delivery of excitation light into the tissue. To boost the Raman signal generation, one would typically have to resort to using a higher light fluence to ensure that the excitation light field sufficiently perfuses the tissue of interest.

However, the absorption measurement scheme outlined above can also be used to perform more efficient Raman measurements. Embodiments of the present invention may first converge on a UPT solution and apply that light field onto the tissue. By suppressing scattering, excitation light may be more uniformly delivered throughout the tissue slab and more Raman emissions can be generated that can then be collected and analyzed.

In one example, this approach may be applied to measure urea concentration as an initial study. Urea has a highly distinctive Raman peak (1003 $cm^{-1}$) to lock onto for measurements. Additional components may include sensing and measuring glucose, triglyceride and hemoglobin count. These components may be measured with phantoms, working progressively towards tissue animal models, and with the eventual goal of applying the technology to humans. This application may enable blood and tissue analysis without needing blood draw.

Process Steps

Figure 13:
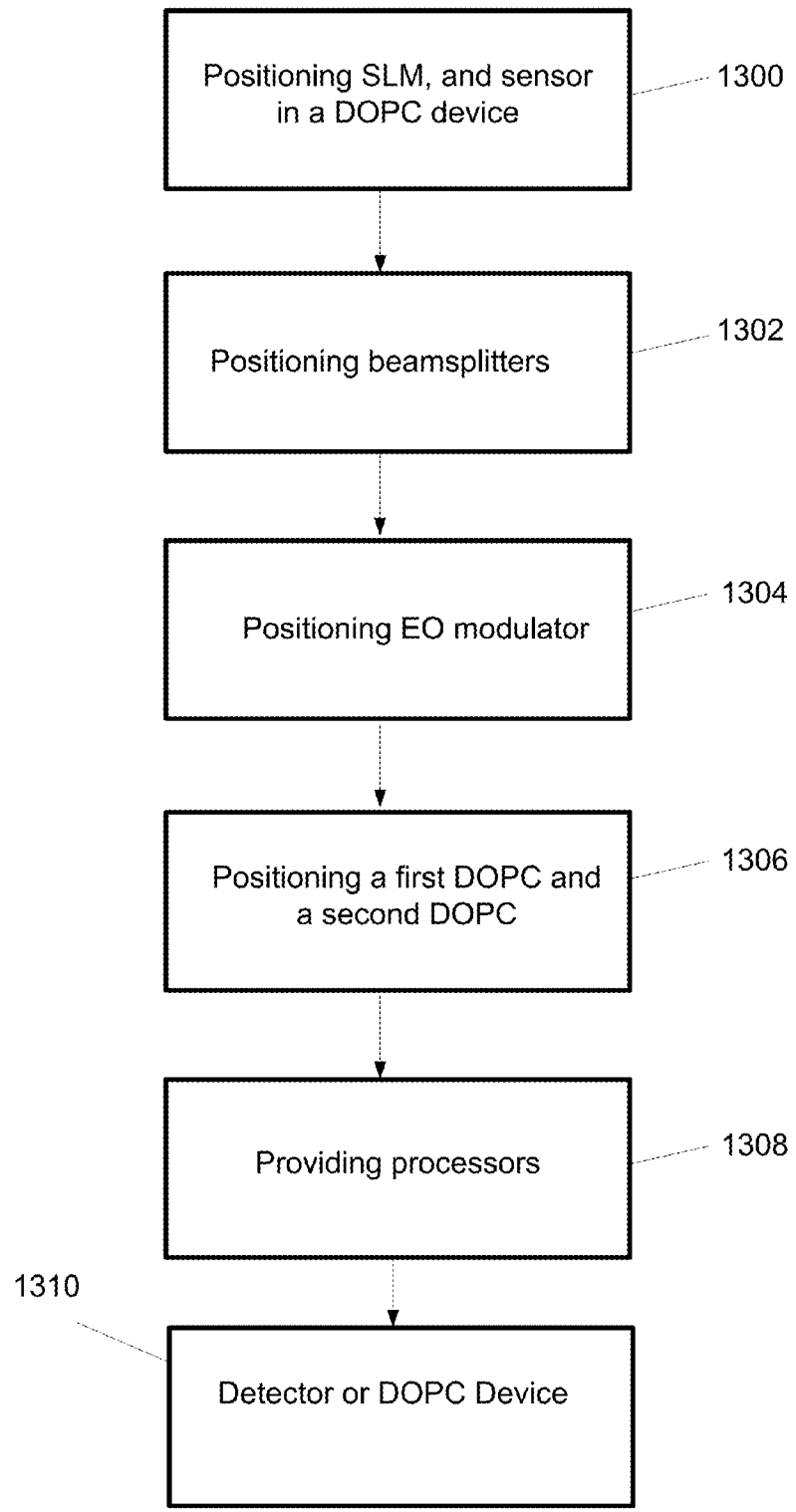
FIG. 13 is a flowchart illustrating a method of fabricating a detector according to one or more embodiments of the present invention.

FIG. 13 is a flowchart illustrating a method of fabricating a DOPC device, or a detector of transmitted light transmitted through a turbid medium, or an imager. The method may comprise the following steps (referring also to elements in FIG. 4(a)-(b), FIG. 6, and FIG. 12).

Block 1300 represents positioning, in one or more DOPC devices (1) a sensor 402 for detecting input light 406 that has been transmitted through the turbid medium 1202 and inputted on the sensor 402; and (2) a SLM 404 for outputting, in response to the input light 406 detected by the sensor 402, output light 410 that is an optical phase conjugate of the input light 406.

The sensor 402 (e.g., wavefront sensor) may comprise a plurality of sensor pixels and the SLM 404 may comprise a plurality of SLM pixels 604 forming a second array. The method may further comprise optically aligning the sensor 402 and the SLM 404 so that each sensor pixel forms a virtual image of the sensor pixel on a corresponding SLM pixel 604.

A first number of the sensor pixels and a second number of the SLM pixels may be such that, when the input light beam 406 is shifted (by a shift), the output light beam 410 shifts by less than $1/1000$ of the shift, or the DOPC device operates at a speed faster than 1 KHz.

One or more pixels 604 of the SLM may be actuated or positioned so that a reference beam 412 reflected off the SLM pixels 604 is modulated to produce a reflected beam 410 having the modified input phases and modified input amplitudes corresponding to the optical phase conjugates of the input phases and the input amplitudes.

The transmitted light may include the output light 410 and the input light 406, and the method may further comprise positioning a holder for supporting the turbid medium such that the transmitted light is transmitted through the turbid medium 1202, wherein the output light that has been transmitted through the turbid medium, and that has retraced a path of the input light through the turbid medium, experiences reduced effects due to scattering by the turbid medium as compared to the input light.

Block 1302 represents positioning a beam splitter 414 to direct the input light 406, and transmit reference light 416, to the sensor 402 so that the input light 406 and the reference light 416 interferes and forms one or more holograms on the sensor 402, the holograms comprising interferometric data.

The SLM 404, sensor 402, and beamsplitter 414 may be positioned such that the beamsplitter 414 is placed at the symmetry plane between the SLM 404 and the sensor 402 and the SLM 404 forms a mirror image onto the sensor 402, and vice versa, wherein the image can be enlarged or shrunk as compared to the actual size of the SLM 404 or sensor 402.

Block 1304 represents positioning an electro-optic modulator 418 to control a relative phase between the input light fields and reference fields of the input light 406 and the reference light 416, respectively, so that the holograms include one or more phase shifted holograms.

Block 1306 represents positioning a first DOPC device (DOPC1) and a second DOPC device (DOPC2), such that the transmitted light 1200, 1204, 1206 propagates between the first DOPC device and the second DOPC device and passes through the turbid medium 1202 each time the transmitted light 1200, 1204, 1206 propagates between the first DOPC device and the second DOPC device, and the output light 1204 from the first DOPC is inputted as the input light 1208 to the second DOPC device. The DOPC devices and the holder may be positioned such that the output light 1210 from the second DOPC device is inputted as the input light 1206 to the first DOPC device.

Block 1308 represents providing one or more processors 408 for calculating absorption and transmission of the transmitted light 1200, 1204, 1206 after one or more passes of the transmitted light 1200, 1204, 1206 through the turbid medium 1202, wherein the absorption and the transmission is calculated from one or more input light fields of the input light 1200 and one or more output light fields of the output light 1204 detected by the DOPC devices (DOPC1 and DOPC2). The processors 408 may calculate the absorption and the transmission of transmitted light 1200, 1204, 1206 that made n passes through the turbid medium 1202, where n is a number of passes that yields between 40% and at least 66% transmission of the transmitted light 1204 as compared to an $(n-1)^{th}$ pass of the transmitted light 1200 and for a turbid medium 1202 that does not absorb the transmitted light 1200, 1204, 1206. The turbid medium 1202 may be biological tissue and the one or more processors may calculate the absorption of the transmitted light 1200, 1204, 1206 as a function of one or more wavelengths of the transmitted light, wherein: (1) the absorption is for matching with data in a database, the data including known absorption as a function of wavelength for one or more medically relevant biochemicals, and (2) the matching identifying an amount of the medically relevant biochemicals in the biological tissue.

The method may further comprise providing one or more processors 408 for receiving the interferometric data and determining input phases and the input amplitudes of input light fields of the input light 406 from the inteferometric data, digitally reversing or modifying the input phases and the input amplitudes to produce reversed or modified input phases and reversed or modified input amplitudes, and outputting the reversed or modified input phases and reversed or modified input amplitudes to the SLM 404 and so that the SLM 404 outputs the output light 410 having the reversed or modified input phases and reversed or modified input amplitudes that are the optical phase conjugates of the input phases and the input amplitudes.

Block 1310 represents the end result of the method, a DOPC device, detector, imager, or scanner. The DOPC device outputs optical phase conjugate light of input light. While the present invention has described using a DOPC device as detector, or as an imager (for viewing objects or images through a turbid medium), the DOPC device is not limited to these applications. The output light, input light, and/or transmitted light may comprise beams of light (e.g., collimated beams), light fields, etc.

Figure 14:
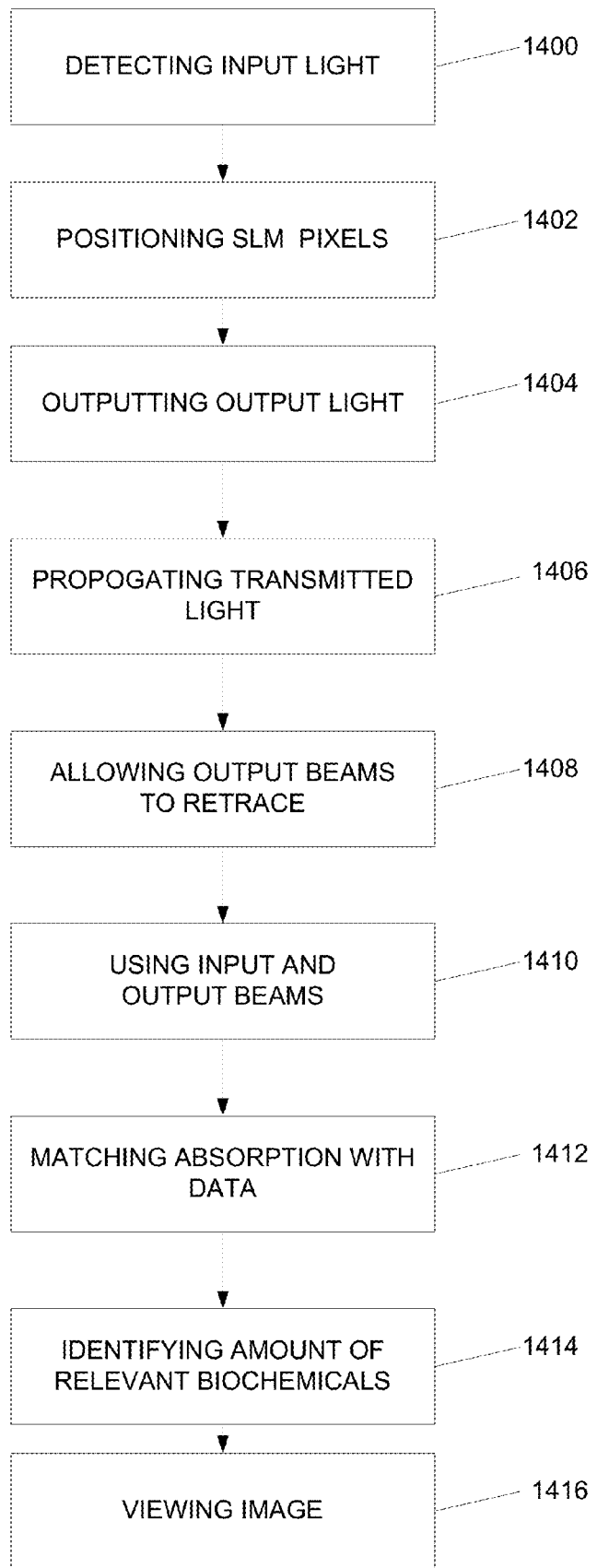
FIG. 14 is a flowchart illustrating a method of detecting light according to one or more embodiments of the present invention.

FIG. 14 is a flowchart illustrating a method for detecting transmitted light transmitted through a turbid medium. The method may comprise the following steps.

Block 1400 represents detecting, on a sensor, the input light beams that have been transmitted through the turbid medium and inputted on the sensor, the input light beams including one or more input light fields.

Block 1402 represents positioning one or more pixels of one or more SLMs so that reference light incident on the pixels is reflected as one or more output light beams having one or more output light fields that are optical phase conjugates of the input light fields detected on the sensor.

Block 1404 represents outputting, from the SLM, in response to the input light beams detected by the sensor, the output light beams having one or more output light fields that are optical phase conjugates of the input light fields. The sensor and the SLM may be in one or more DOPC devices.

The turbid medium may be biological tissue, the transmitted light may include the output light beams and the input light beams, and the DOPC devices may include a first DOPC device and a second DOPC device.

Block 1406 represents propagating the transmitted light between the first DOPC device and the second DOPC device so that the transmitted light passes through the turbid medium each time the transmitted light propagates between the first DOPC device and the second DOPC device, the output light beams from the first DOPC are inputted as the input light beams to the second DOPC device, and the output light beams from the second DOPC device are inputted as the input light beams to the first DOPC device.

The transmitted light may make n passes through the turbid medium, wherein the output light comprises n first output beams from the first DOPC device and n−1 second output beams from the second DOPC device, the input light comprises n first input beams to the first DOPC device and n second input beams to the second DOPC device, the $j^{th}$ first output beam is inputted as the $j^{th}$ second input beam and the $j^{th}$ second output beam is inputted as the $j+1^{th}$ first input beam, and the j=1 input beam being supplied by an external light source.

Block 1408 represents allowing the output light beams to retrace one or more paths of the input light beams through the turbid medium, the output light beams experiencing suppressed effects of scattering by the turbid medium as compared to scattering of the input light beams by the turbid medium.

Block 1410 represents using the input light fields and the output light fields to measure absorption ("measured absorption") of the transmitted light by the biological tissue as a function of one or more wavelengths of the light.

Block 1412 represents matching the absorption with data in a database, the data including known absorption as a function of wavelength for one or more medically relevant biochemicals.

Block 1414 represents identifying an amount of the medically relevant biochemicals in the biological tissue based on a comparison of the measured absorption with the known absorption. The turbid medium may scatter light at least 200 times in one pass of the transmitted light beam through the turbid medium.

Block 1416 represents viewing an image through the turbid medium using the output light fields.

Advantages and Improvements

In summary, embodiments of the invention provide the principle, design, and implementation of a DOPC method that includes a novel and versatile technique for generating OPC waves. As compared to conventional OPC methods that rely on nonlinear light-matter interactions, DOPC may work with both CW and pulsed laser systems of various wavelengths and power levels. One limitation of the DOPC method is that the update rate is determined by the speed of the wavefront measurement combined with the update rate of the SLM employed. With high-speed commercially available devices, one may achieve an update rate close to 1 kHz—a speed that is slow compared to Brillouin scattering based OPC systems but that is significantly faster than methods based on commonly used photorefractive crystals, such as $BaTiO_3$.

An additional advantage of DOPC is that the phase conjugate reflectivity can be arbitrarily controlled since the phase conjugate power is independent of the input signal power. This property provides an advantage over nonlinear optics based OPC systems.

The degrees of freedom handled by DOPC ($\sim 10^6$) are significantly greater than many adaptive optics systems, comparable to the pixel by pixel optimization method but with a much shorter measurement time.

Theoretical analysis and experimental tests further illustrate that DOPC in random scattering media is a surprisingly robust process against phase errors. This result suggests that phase accuracy can be reasonably sacrificed to improve other aspects of the experiments such as the speed and the degrees of freedom capacity. This finding is of significant importance to many adaptive optics based techniques. Accordingly, DOPC may be utilized in a broad range of applications in biomedical optics.

Application: Improved High-Resolution 3D Microscopes and Deep Tissue Biochemical Imaging Embodiments of the invention may use the TSOPC effect to improve and simplify a high-resolution 3D microscopy method known as 4Pi microscopy [12]. 4Pi microscopy is an imaging method in which two counter-propagating laser beams are tightly focused onto the same spatial spot. By raster-scanning this mutual focal spot over a sample and collecting the generated fluorescence signal from fluorophores excited within this focal spot, a high-resolution image of the sample can be rendered. The lateral resolution of such a system is defined by the focal spot diameter. The two counter-propagating light beams mutually interfere along the axial direction. The resulting axial standing interference pattern and the point spread function of the focal spot define the axial resolution. The lateral and axial resolution can be as high as 200 nm and 120 nm respectively. This type of microscopy system has a higher axial resolution than the more commonly used confocal microscope system which typically has an axial resolution of 600 nm.

Despite its resolution advantage over confocal microscopy, 4Pi microscopy is seldom used because the foci of the two beams need to be precisely aligned to each other. The usage of 4Pi microscopy is also restrictive for two reasons. First, bulk refractive index variations of a sample can deflect and misalign the two propagating beams—a good 4Pi microscope system must constantly correct for such misalignment during imaging. Second, tissue scattering can significantly distort one or both of the laser beams and prevent the forming of a good focal spot. This actually limits the tissue thickness we can use with 4Pi microscopy.

Figure 15:
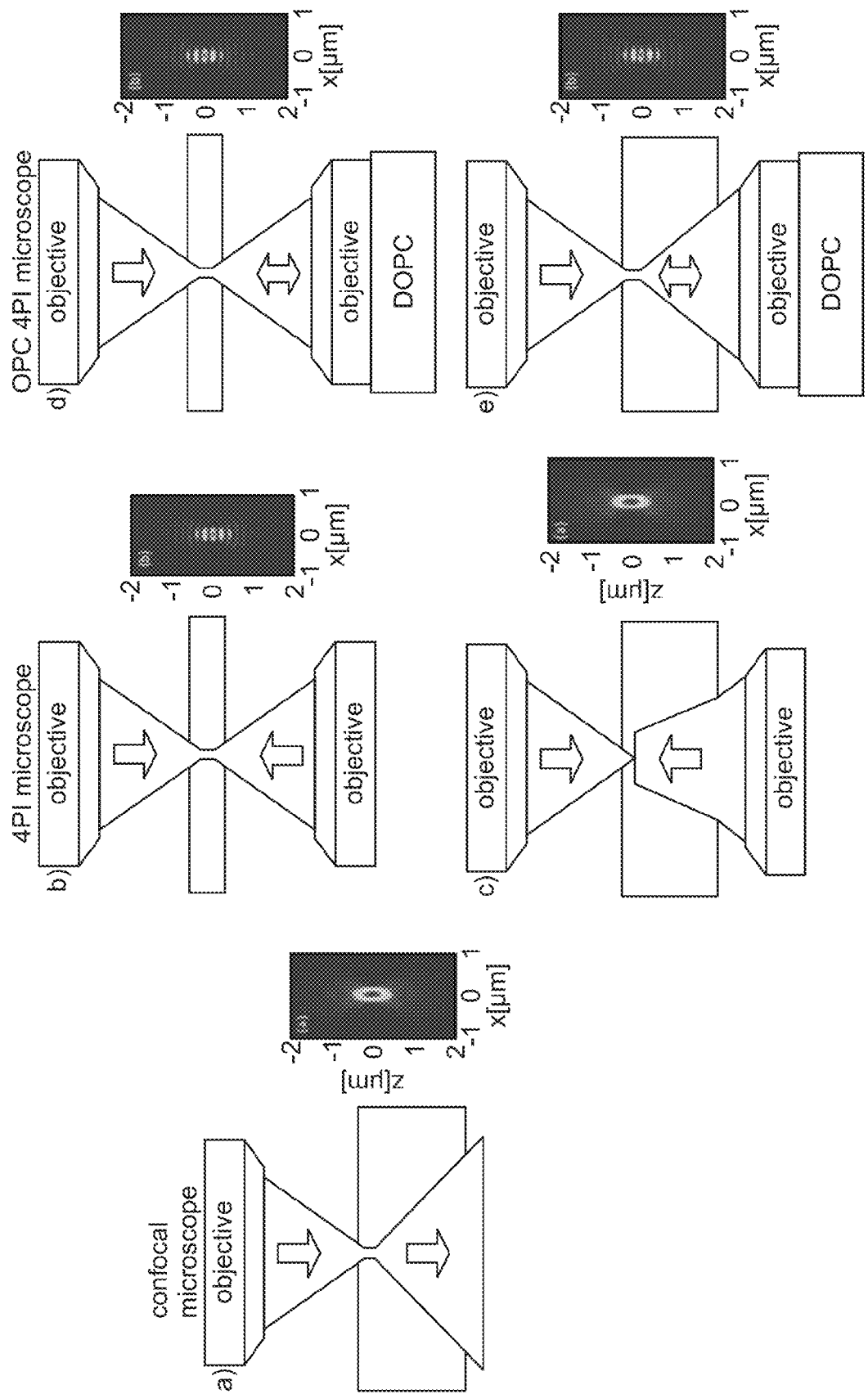
FIG. 15 (a) illustrates a confocal microscope that uses a tightly focused laser to perform a high-resolution scan, wherein the axial resolution is relatively poor (~600 nm)

The self-correcting nature of the TSOPC effect can be used to address these two weaknesses. A viable optical phase conjugation assisted 4Pi (OPC 4Pi) microscopy scheme is shown in FIG. 15*d*. A tightly focused laser beam is launched into the sample from one side. The transmission is then collected and measured with the DOPC system. The DOPC system then launches a time-reversed version of the light field back through the sample. Due to the TSOPC effect, the returning beam retraces the original transmission path and automatically comes to a focus at the same location as the original beam's focus. An OPC 4Pi system can effectively self-align and thereby eliminate the primary implementation challenge of 4Pi microscopy. In addition, the ability of TSOPC to correct for scattering also means that the an OPC 4Pi microscope can be used to image through thicker samples. In fact, an OPC 4Pi system may be able to image to the same depth as a confocal microscope for samples of arbitrary thickness (thickness limited only by the efficiency of the TSOPC reconstruction) (see FIG. 15*e*).

The TSOPC effect can be used to suppress scattering effects that plague existing optical imaging techniques, and thereby improve their performance. Accordingly, the OPC 4Pi microscopy method of one or more embodiments of the invention is a good example. On a different front, the TSOPC effect can also be adapted to create entirely new classes of imaging systems.

Application: Acoustic Assisted Phase Conjugate Optical Tomography

Figure 16:
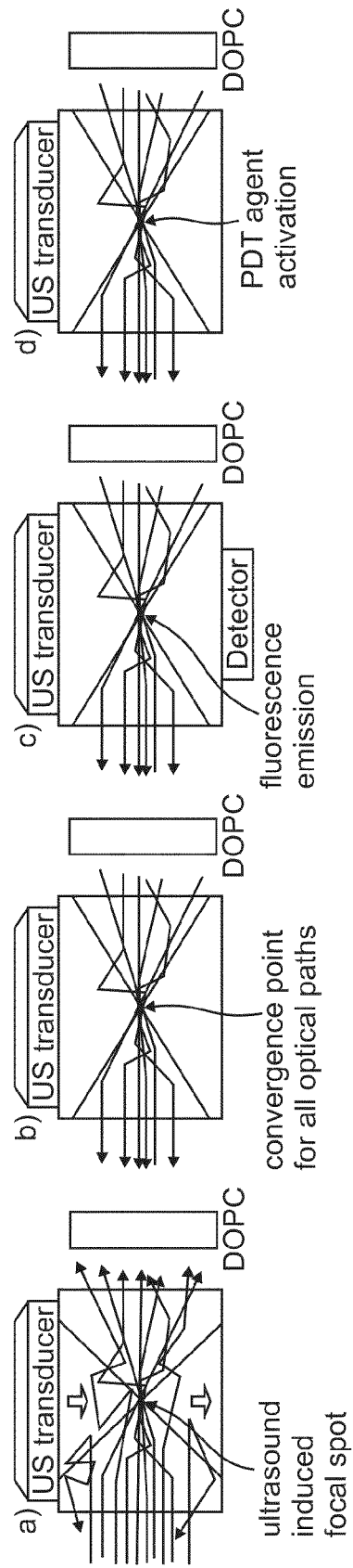
FIG. 16 illustrates the TSOPC based optical focal spot generator, according to one or more embodiments of the present invention, wherein in FIG. 16(*a*) an ultrasound transducer (frequency=f) focuses acoustic power into a desired spatial point and the DOPC locks onto and records the light field components (upshifted by f) that have passed through that focal point, FIG. 16(*b*) illustrates the DOPC generating a light field that must pass through that focal point—effectively focusing light onto that point, FIG. 16(*c*) illustrates that the focal point can be used to excite fluorophores for imaging purposes, and FIG. 16(*d*) illustrates the focal point can also be used to locally excite PDT agent deep within the tissue.

Embodiments of the present invention may be used in an imaging scheme based on TSOPC is shown in FIG. 16 *a-c*. An ultrasound wave of frequency f is tightly focused into a spot of interest within the tissue. Since the ultrasound wave experiences comparatively weaker scattering in tissues than the optical transmission, a well-defined ultrasound focal spot of dimension ~100 microns or better is created deep within the tissue. Next, a weak light beam (scouting field) is transmitted through the sample. A portion of the photons that pass through the ultrasound focal zone are frequency upshifted or downshifted by f (due to absorption or stimulated emission of an ultrasound phonon). The photons passing through other regions where the ultrasound wave is traversing may also be frequency shifted but the upshift is most efficient within the focal zone (where the ultrasound intensity is highest). (A related approach—ultrasound modulated optical tomography [13] detects these photons to determine tissue absorption at that location.) The DOPC system is then applied to record the light field pattern of these transmitted upshifted photons. Such an application can be accomplished by upshifting the reference beam of the wavefront sensing system by the ultrasound frequency so that the reference beam only interacts interferometrically with the upshifted transmission component. By playing back a high intensity OPC field (focusing field) based on this set of data, embodiments of the invention are able to preferentially send photons back along the optical paths that intersect with the focal zone. In effect, this methodology offers a way to focus light at an arbitrarily definable location within the tissue. Embodiments of the invention simply focus the ultrasound waves at the location of interest and the proposed system will channel the light into that location.

This system is unique in two ways. First, this system provides an unprecedented ability to focus light at deep locations (potentially to depths of ~cm's and a focal zone of dimension ~100 microns; there is a trade-off between depth and resolution) within tissues. Tissue scattering typically limits a conventional focusing system's (such as a simple lens) ability to focus light within tissue to a couple of mm's at best. Second and more importantly, this focal spot can be moved and scanned freely within the tissue by maneuvering the ultrasound focal spot accordingly.

By raster scanning this focal spot within the tissue and measuring either the spontaneous Raman signal or the fluorescence emission generated for each spot location, a biochemical image of the tissue can be created. Results indicate that this method may be used for tissue of thickness up to ~2 cm (torso thickness of a mouse). This approach would be useful for small animal studies where biochemical changes can be imaged and mapped with good resolution. There is no theoretical or experimentally established limit that indicates that this method is not usable for tissue of greater thickness.

Application: Improved Photodynamic Therapy

Embodiments of the invention may be applied to the TSOPC effect to improve optical based therapeutic procedures, such as photodynamic therapy (PDT) [14]. In PDT, a photosensitizing agent, such as Photofrin™, is introduced into the body and preferentially uptaken by cancer cells. Next, the tissue is illuminated with light to activate the photosensitizing agent. The resulting biochemical reactions then induce apoptosis of the cancer cells. The typical depth of necrosis with PDT is ~4 mm. Much of the delivered light does not penetrate through the tissue due to scattering. Furthermore, the procedure is fairly indiscriminate in its light delivery—the specificity of the treatment is almost entirely dependent on preferential uptake of the PDT agent by cancer cells.

The ultrasound guided light focusing strategy described above can be applied in PDT procedures to provide the much needed ability to focus and steer light onto specific locations in tissues (see FIG. 16d). The feasibility of this approach for targeted PDT agent activation progressively may be evaluated in tissue models and animal models.

Advantages

Advantages and ability tin innovate are frequently driven by the discovery of new effects and phenomena. New phenomena typically introduce new tools and concepts into a scientist's repertoire. In turn, these tools and concepts can form the basis of new technologies for solving challenges that were previously insurmountable. In this fashion, the TSOPC phenomenon of embodiments of the present invention can provide the opportunity to tackle numerous unresolved biomedical challenges in a new light.

Traditionally, it is known that light scattering in tissue cannot be nullified in any meaningful way. Despite the deleterious impact that scattering has on optical tissue analysis methodologies, current strategies for dealing with tissue scattering are generally focused on circumventing the issue and/or minimizing its impact. The ability of time-reversal techniques to correct for light field distortions is known in the optical community. However, the idea of undoing tissue turbidity by using time-reversal was largely ignored by the research community because it was perceived as too difficult and extraordinarily stringent. However, embodiments of the invention have shown that this perception is actually incorrect and that this type of scattering suppression for biological tissues is surprisingly robust. Accordingly, embodiments of the invention may be adapted for highly novel and useful biomedical applications—applications that would not have been possible without the use of the TSOPC effect.

The ability to clear scattering provides the ability to make direct and potentially highly sensitive absorption and Raman measurements in tissues. This can change the way one addresses the challenge of making sufficiently sensitive and non-invasive biochemical (including glucose) sensors. The concept applies well to the detection of other biochemicals within tissues as well. Further options include the ability to perform blood analysis methods that do not require blood draws.

The self-correcting nature of TSOPC is also helpful in allowing the construction of better imaging systems. For example, the TSOPC can be used to simplify and improve the performance of high resolution 4Pi microscopes. TSOPC can also be helpful in focusing light deep within tissues for imaging applications. Additional imaging uses for TSOPC may also be available. Finally, the ability to deliver light efficiently through tissues is an advantage unique to TSOPC. This ability may allow photodynamic therapy methods to reach tissue depths that are unprecedented.

In addition, the remarkable absence of resolution loss during TSOPC reconstruction is a feature that may be used for high-resolution deep tissue imaging.

References

The following references are incorporated by reference herein.

1. M. Wenner, "The most transparent research," Nat. Med. 15(10), 1106-1109 (2009).

2. L. V. Wang, "Multiscale photoacoustic microscopy and computed tomography," Nat. Photonics 3(9), 503-509 (2009).

3. I. M. Vellekoop, and A. P. Mosk, "Universal optimal transmission of light through disordered materials," Phys. Rev. Lett. 101(12), 120601 (2008).

4. Z. Yaqoob, D. Psaltis, M. S. Feld, and C. Yang, "Optical phase conjugation for turbidity suppression in biological samples," Nat. Photonics 2(2), 110-115 (2008).

5. I. M. Vellekoop, and A. P. Mosk, "Focusing coherent light through opaque strongly scattering media," Opt. Lett. 32(16), 2309-2311 (2007).

6. I. M. Vellekoop, E. G. van Putten, A. Lagendijk, and A. P. Mosk, "Demixing light paths inside disordered metamaterials," Opt. Express 16(1), 67-80 (2008).

7. M. Cui, E. J. McDowell, and C. H. Yang, "Observation of polarization-gate based reconstruction quality improvement during the process of turbidity suppression by optical phase conjugation," Appl. Phys. Lett. 95(12), 123702 (2009).

8. M. Cui, E. J. McDowell, and C. Yang, "An in vivo study of turbidity suppression by optical phase conjugation (tsopc) on rabbit ear," Opt. Express 18(1), 25-30 (2010).

9. A. Yariv, and P. Yeh, "Phase conjugate optics and real-time holography," IEEE J. Quantum Electron. 14(9), 650-660 (1978).

10. J. Feinberg, and R. W. Hellwarth, "Phase-conjugating mirror with continuous-wave gain," Opt. Lett. 5(12), 519-521 (1980).

11. R. C. Lind, and D. G. Steel, "Demonstration of the longitudinal modes and aberrationcorrection properties of a continuous-wave dye laser with a phase-conjugate mirror," Opt. Lett. 6(11), 554-556 (1981).

12. I. Lindsay, "Specular reflection cancellation enhancement in the presence of a phase-conjugate mirror," J. Opt. Soc. Am. B 4(11), 1810-1815 (1987).

13. D. M. Pepper, "Observation of diminished specular reflectivity from phase-conjugate mirrors," Phys. Rev. Lett. 62(25), 2945-2948 (1989).

14. P. Yeh, Introduction to photorefractive nonlinear optics (John Wiley & Sons, Inc, New York, 1993).

15. D. P. M. Gower, Optical phase conjugation (Springer-Verlag, New York, 1994).

16. C. A. Primmerman, D. V. Murphy, D. A. Page, B. G. Zollars, and H. T. Barclay, "Compensation of atmospheric optical distortion using a synthetic beacon," Nature 353(6340), 141-143 (1991).

17. M. J. Booth, M. A. A. Neil, R. Juskaitis, and T. Wilson, "Adaptive aberration correction in a confocal microscope," Proc. Natl. Acad. Sci. U.S.A. 99(9), 5788-5792 (2002).

18. M. Rueckel, J. A. Mack-Bucher, and W. Denk, "Adaptive wavefront correction in two-photon microscopy using coherence-gated wavefront sensing," Proc. Natl. Acad. Sci. U.S.A. 103(46), 17137-17142 (2006).

19. D. Débarre, E. J. Botcherby, T. Watanabe, S. Srinivas, M. J. Booth, and T. Wilson, "Image-based adaptive optics for two-photon microscopy," Opt. Lett. 34(16), 2495-2497 (2009).

20. D. Débarre, E. J. Botcherby, M. J. Booth, and T. Wilson, "Adaptive optics for structured illumination microscopy," Opt. Express 16(13), 9290-9305 (2008).

21. Z. Yaqoob, D. Psaltis, M. S. Feld, and C. Yang, "Optical phase conjugation for turbidity suppression in biological samples" Nature Photonics, vol. 2, pp. 110-115, 2008.

22. M. Cui, E. McDowell, and C. Yang, "Observation of polarization-gate based reconstruction quality improvement during the process of turbidity suppression by optical phase conjugation," Applied Physics Letters, vol. 95, p. 123702, 2009.

23. E. N. Leith and J. Upatneiks, "Holographic imagery through diffusing media," JOSA, vol. 56, p. 523, 1966.

24. M. Wenner, "The most transparent research," Nature Medicine, vol. 15, p. 1106, 2009.

25. T. Vo-Dinh, Biomedical Photonics Handbook. Boca Raton, Fla.: CRC Press, 2003.

26. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical Coherence Tomography," Science, vol. 254, pp. 1178-1181, Nov. 22, 1991.

27. D. A. Boas, D. H. Brooks, E. L. Miller, C. A. DiMarzio, M. Kilmer, R. J. Gaudette, and Q. Zhang, "Imaging the body with diffuse optical tomography," IEEE Signal Processing, vol. 18, pp. 57-75, 2001.

28. E. Jakeman and K. D. Ridley, "Incomplete phase conjugation through a random phase screen. II. Numerical simulations," JOSA A, vol. 13, p. 2293, 1996.

29. S. C. W. Hyde, R. Jones, N. P. Barry, J. C. Dainty, P. M. W. French, K. M. Kwolek, D. D. Nolte, and M. R. Melloch, "Depth-resolved holography through turbid media using photorefraction," IEEE JSTQE, vol. 2, pp. 965-975, 1996.

30. I. Vellokoop and A. Mosk, "Universal Optimal Transmission of Light Through Disordered Materials," Phys. Rev. Lett., vol. 101, p. 120601, 2008.

31. M. Fink, "Time-reversed acoustics," Scientific American, vol. 281, pp. 91-97, November 1999.

32. S. Hell and E. Stelzer, "Properties of a 4pi confocal fluorescence microscope.," JOSA A, vol. 9, p. 2159, 1992.

33. L. Wang and X. Zhao, "Ultrasound-modulated optical tomography of absorbing objects buried in dense tissue-simulating turbid media," Applied Optics, vol. 36, p. 7277, 1997.

34. T. J. Dougherty, C. J. Gomer, B. W. Henderson, G. Joni, D. Kessel, M. Korbelik, J. Moan, and Q. Peng, "Photodynamic therapy," Journal of the National Cancer Institute, vol. 90, pp. 889-905, June 1998.

35. X. Cui, L. M. Lee, X. Heng, W. Zhong, P. W. Sternberg, D. Psaltis, and C. Yang, "Lensless high-resolution on-chip optofluidic microscopes for Caenorhabditis elegans and cell imaging," PNAS, vol. 105, p. 10670, 2008.

36. E. Check Hayden, "Microscopic marvels: Microscope for the masses," Nature, vol. 459, p. 632, 2009.

37. M. Fink, "Time reversed acoustics," Phys. Today 50(3), 34-40 (1997).

38. M. Fink, "Time-reversed acoustics," Sci. Am. 281(5), 91-97 (1999).

39. I. Yamaguchi, and T. Zhang, "Phase-shifting digital holography," Opt. Lett. 22(16), 1268-1270 (1997).

40. T. Zhang, and I. Yamaguchi, "Three-dimensional microscopy with phase-shifting digital holography," Opt. Lett. 23(15), 1221-1223 (1998).

41. A. Derode, A. Tourin, and M. Fink, "Random multiple scattering of ultrasound. Ii. Is time reversal a self-averaging process?" Phys. Rev. E Stat. Nonlin. Soft Matter Phys. 64(3), 036606 (2001).

42. J. W. Goodman, "Some fundamental properties of speckle," J. Opt. Soc. Am. 66(11), 1145-1150 (1976).

42. Y. Kawata et. al, "4-Pi confocal optical system with phase conjugation," Optics letters, Vol. 21. No. 18, pages 1415-1417, Sep. 15, 1996.

43. Meng Cui and Changhuei Yang, "Implementation of a digital optical phase conjugation system and its application to study the robustness of turbidity suppression by phase conjugation," Optics Express, Vol. 18, No. 4, published 2 Feb. 2010.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A detector of transmitted light that has been transmitted through a turbid medium, comprising:
one or more Digital Optical Phase Conjugation (DOPC) devices, wherein the DOPC devices include:
a sensor for detecting interference of reference light with input light, wherein the input light has been transmitted through the turbid medium and inputted on the sensor;
one or more processors for:
determining one or more input phases of the input light from the interference;
modifying the input phases to produce optical phase conjugates of the input phases; and
a spatial light modulator (SLM) for outputting, in response to the input light detected by the sensor, output light that is generated from the optical phase conjugates of the input light.

2. The detector of claim 1, wherein the transmitted light includes the output light and the input light, the detector further comprising:
a holder for supporting the turbid medium and positioned such that the transmitted light is transmitted through the turbid medium, wherein the output light that has been transmitted through the turbid medium, and that has retraced a path of the input light through the turbid medium, experiences reduced effects due to scattering by the turbid medium as compared to the input light.

3. The detector of claim 2, wherein:
the DOPC devices include a first DOPC device and a second DOPC device;
the DOPC devices and the holder are positioned such that the transmitted light propagates between the first DOPC device and the second DOPC device and passes through the turbid medium each time the transmitted light propagates between the first DOPC device and the second DOPC device, and
the output light from the first DOPC is inputted as the input light to the second DOPC device.

4. The detector of claim 3, wherein the DOPC devices and the holder are positioned such that the output light from the second DOPC device is inputted as the input light to the first DOPC device.

5. The detector of claim 4, further comprising one or more processors for calculating absorption and transmission of the transmitted light after one or more passes of the transmitted light through the turbid medium, wherein the absorption and the transmission is calculated from one or more input light fields of the input light and one or more output light fields of the output light detected by the DOPC devices.

6. The detector of claim 5, wherein the processors calculate the absorption and the transmission of the transmitted light that made n passes through the turbid medium, where n is a number of passes that yields between 40% and at least 66% transmission of the transmitted light as compared to an $(n-1)^{th}$ pass and for a turbid medium that does not absorb the transmitted light.

7. The detector of claim 5, wherein:
the turbid medium is biological tissue and the one or more processors calculate the absorption of the transmitted light as a function of one or more wavelengths of the transmitted light;
the absorption is for matching with data in a database, the data including known absorption as a function of wavelength for one or more medically relevant biochemicals, and the matching identifies an amount of the medically relevant biochemicals in the biological tissue.

8. The detector of claim 1, further comprising:
a beam splitter positioned to direct the input light, and transmit the reference light, to the sensor so that the input light and the reference light interferes and forms the interference comprising one or more holograms on the sensor, the holograms comprising interferometric data; and
the one or more processors for:
receiving the interferometric data and determining the input phases and input amplitudes of input light fields of the input light from the inteferometric data;
digitally modifying the input phases and the input amplitudes to produce modified input phases and modified input amplitudes; and
outputting the modified input phases and modified input amplitudes to the SLM and so that the SLM outputs the output light having the modified input phases and modified input amplitudes that are the optical phase conjugates of the input phases and the input amplitudes.

9. The detector of claim 8, further comprising an electro-optic modulator that controls a relative phase between the input light fields of the input light and reference fields of the reference light, so that the holograms include one or more phase shifted holograms.

10. The detector of claim 1, wherein:
the sensor comprises a plurality of sensor pixels,
the SLM comprises a plurality of SLM pixels forming a second array, and
the sensor and the SLM are optically aligned so that each sensor pixel forms a virtual image of the sensor pixel on a corresponding SLM pixel.

11. The detector of claim 1, wherein the output light is used to view an object through the turbid medium, and the output light forms an image of the object that is clearer than an image formed without the DOPC device.

12. A method of fabricating a detector of transmitted light transmitted through a turbid medium, comprising:
positioning and connecting, in one or more Digital Optical Phase Conjugation (DOPC) devices:
a sensor for detecting interference of reference light with input light, wherein the input light has been transmitted through the turbid medium and inputted on the sensor;
one or more processors for:
determining one or more input phases of the input light from the interference;
modifying the input phases to produce optical phase conjugates of the input phases; and
a spatial light modulator (SLM) for outputting, in response to the input light detected by the sensor, output light that is generated from the optical phase conjugates of the input light, wherein the output light experiences reduced effects due to scattering by the turbid medium as compared to the input light.

13. The method of claim 11, wherein the transmitted light includes the output light and the input light, the method further comprising
positioning a holder for supporting the turbid medium such that the transmitted light is transmitted through the turbid medium, wherein the output light that has been transmitted through the turbid medium, and that has retraced a path of the input light through the turbid medium, experiences reduced effects due to scattering by the turbid medium as compared to the input light.

14. The method of claim 12, wherein the DOPC devices include a first DOPC device and a second DOPC device, the method further comprising:

positioning the DOPC devices and the holder such that:

the light propagates between the first DOPC device and the second DOPC device and passes through the turbid medium each time the transmitted light propagates between the first DOPC device and the second DOPC device, and the output light from the first DOPC is inputted as the input light to the second DOPC device.

15. The method of claim 14, further comprising positioning the DOPC devices and the holder such that the output light from the second DOPC device is inputted as the input light to the first DOPC device.

16. The method of claim 15, further comprising providing one or more processors for calculating absorption and transmission of the transmitted light after one or more passes of the transmitted light through the turbid medium, wherein the absorption and the transmission is calculated from one or more input light fields of the input light and one or more output light fields of the output light detected by the DOPC devices.

17. The method of claim 16, wherein the processors calculate the absorption and the transmission of transmitted light that made n passes through the turbid medium, where n is a number of passes that yields between 40% and at least 66% transmission of the light as compared to an $(n-1)^{th}$ pass and for a turbid medium that does not absorb the transmitted light.

18. The method of claim 16, wherein the turbid medium is biological tissue and the one or more processors calculate the absorption of the transmitted light as a function of one or more wavelengths of the transmitted light, wherein:

(1) the absorption is for matching with data in a database, the data including known absorption as a function of wavelength for one or more medically relevant biochemicals, and (2) the matching identifying an amount of the medically relevant biochemicals in the biological tissue.

19. The method of claim 12, further comprising:

positioning a beam splitter to direct the input light, and transmit the reference light, to the sensor so that the input light and the reference light interferes and forms the interference comprising one or more holograms on the sensor, the holograms comprising interferometric data; and providing one or more processors for:

receiving the interferometric data and determining the input phases and the input amplitudes of input light fields of the input light from the inteferometric data, digitally modifying the input phases and the input amplitudes to produce modified input phases and reversed input amplitudes; and outputting the modified input phases and the modified input amplitudes to the SLM and so that the SLM outputs the output light having the modified input phases and modified input amplitudes that are the optical phase conjugates of the input phases and the input amplitudes.

20. The method of claim 19, further comprising positioning an electro-optic modulator to control a relative phase between the input light fields of the input light and reference fields of the reference light, so that the holograms include one or more phase shifted holograms.

21. The method of claim 12, wherein the sensor comprises a plurality of sensor pixels and the SLM comprises a plurality of SLM pixels forming a second array, the method further comprising optically aligning the sensor and the SLM so that each sensor pixel forms a virtual image of the sensor pixel on a corresponding SLM pixel.

22. The method of claim 12, wherein the output light is used to view an object through the turbid medium, and the output light forms an image of the object that is clearer than an image formed without the DOPC device.

23. A method for detecting transmitted light transmitted through a turbid medium, comprising:

interfering reference light with one or more input light beams to form interference, wherein the input light beams have been transmitted through the turbid medium, inputted on the sensor, and include one or more input light fields;

detecting the interference on a sensor;

determining, in one or more processors, one or more input phases of the input light from the interference;

modifying, in the one or more processors, the input phases to produce optical phase conjugates of the input phases; and outputting, from a spatial light modulator (SLM), in response to the input light beams detected by the sensor, one or more output lights beams having one or more output light fields that are the optical phase conjugates of the input light fields, wherein the sensor and the SLM are in one or more digital optical phase conjugation (DOPC) devices.

24. The method of claim 23, wherein the turbid medium is biological tissue, the transmitted light includes the output light beams and the input light beams, and the DOPC devices include a first DOPC device and a second DOPC device, the method further comprising:

propagating the transmitted light between the first DOPC device and the second DOPC device so that:

the transmitted light passes through the turbid medium each time the transmitted light propagates between the first DOPC device and the second DOPC device, the output light beams from the first DOPC are inputted as the input light beams to the second DOPC device, and the output light beams from the second DOPC device are inputted as the input light beams to the first DOPC device;

using the input light fields and the output light fields to measure absorption ("measured absorption") of the transmitted light by the biological tissue as a function of one or more wavelengths of the light;

matching the absorption with data in a database, the data including known absorption as a function of wavelength for one or more medically relevant biochemicals, and identifying an amount of the medically relevant biochemicals in the biological tissue based on a comparison of the measured absorption with the known absorption.

25. The method of claim 23, wherein the turbid medium scatters the transmitted light at least 200 times in one pass of the transmitted light through the turbid medium, the method further comprising:

viewing an image through the turbid medium using the output light fields.

26. A phase conjugating device, comprising:

a sensor for measuring interference of a reference wave with an input wave, wherein the input wave has been transmitted through a scattering medium;

one or more processors for:
    determining one or more phases of the input wave from the interference;
    modifying the phases to produce one or more phase conjugates of the phases; and
a spatial light modulator (SLM) for outputting one or more output waves generated from the phase conjugates.

* * * * *